(12) United States Patent
Bally et al.

(10) Patent No.: US 8,709,474 B2
(45) Date of Patent: Apr. 29, 2014

(54) LIPOSOMES WITH IMPROVED DRUG RETENTION FOR TREATMENT OF CANCER

(71) Applicant: BC Cancer Agency, Vancouver (CA)

(72) Inventors: Marcel Bally, Bowen Island (CA); Euan Ramsay, Vancouver (CA)

(73) Assignee: BC Cancer Agency, Vancouver (CA)

(*) Notice: Subject to any disclaimer, the term of this patent is extended or adjusted under 35 U.S.C. 154(b) by 0 days.

(21) Appl. No.: 13/709,005

(22) Filed: Dec. 9, 2012

(65) Prior Publication Data

US 2013/0136790 A1 May 30, 2013

Related U.S. Application Data

(62) Division of application No. 11/576,595, filed as application No. PCT/CA2005/001536 on Oct. 6, 2005, now Pat. No. 8,349,360.

(60) Provisional application No. 60/615,943, filed on Oct. 6, 2004.

(51) Int. Cl.
*A61K 9/127* (2006.01)
*A61K 31/4745* (2006.01)

(52) U.S. Cl.
USPC .......................................... 424/450; 514/283

(58) Field of Classification Search
None
See application file for complete search history.

(56) References Cited

U.S. PATENT DOCUMENTS

| | | | |
|---|---|---|---|
| 4,310,506 A | 1/1982 | Baldeschwieler et al. | |
| 5,192,549 A | 3/1993 | Barenolz et al. | |
| 5,316,771 A | 5/1994 | Barenholz et al. | |
| 5,352,435 A | 10/1994 | Unger | |
| 5,525,232 A | 6/1996 | Veiro et al. | |
| 5,616,341 A | 4/1997 | Mayer et al. | |
| 5,736,155 A | 4/1998 | Bally et al. | |
| 5,785,987 A | 7/1998 | Hope et al. | |
| 5,837,282 A * | 11/1998 | Fenske et al. | 424/450 |
| 6,106,858 A | 8/2000 | Ye et al. | |
| 6,110,491 A | 8/2000 | Kirpotin | |
| 6,723,338 B1 * | 4/2004 | Sarris et al. | 424/450 |
| 7,238,367 B2 | 7/2007 | Tardi et al. | |
| 7,744,921 B2 | 6/2010 | Tardi et al. | |
| 7,811,602 B2 | 10/2010 | Cullis et al. | |
| 2003/0091621 A1 * | 5/2003 | Tardi et al. | 424/450 |
| 2006/0008909 A1 | 1/2006 | Cullis et al. | |
| 2006/0154848 A1 | 7/2006 | Girboux et al. | |

FOREIGN PATENT DOCUMENTS

| | | |
|---|---|---|
| CA | 2527130 | 10/2004 |
| CA | 2536612 | 10/2004 |
| WO | WO 9300888 | 1/1993 |
| WO | WO 9625147 | 8/1996 |
| WO | WO 9818450 | 5/1998 |
| WO | WO01/85131 A2 * | 11/2001 |
| WO | WO0185131 | 11/2001 |
| WO | WO03011345 | 2/2003 |
| WO | WO03022250 | 3/2003 |
| WO | WO03028696 | 4/2003 |
| WO | WO03028697 | 4/2003 |
| WO | WO2004008794 | 1/2004 |
| WO | WO2004087104 | 10/2004 |
| WO | WO2004087115 | 10/2004 |

OTHER PUBLICATIONS

U.S. Appl. No. 60/362,074, filed Mar. 7, 2002, Tardi et al.
Abraham et al. "An evaluation of transmembrane ion gradient-mediated encapsulation of topotecan within liposomes" J Control Release. May 18, 2004;96(3):449-61.
Baker J et al. "Irinophore C, a Novel Nanoformulation of Irinotecan, Alters Tumor Vascular Function and Enhances the Distribution of 5-Fluorouracil and Doxorubicin" Clin Cancer Res. Nov. 15, 2008;14(22):7260-71.
Messerer C L et al. "Liposomal Irinotecan: Formulation Development and Therapeutic Assessment in Murine Xenograft Models of Colorectal Cancer" Clin Cancer Res. Oct. 1, 2004;10(19):6638-49.
Patankar N et al. "The Role of the Transition Metal Copper and the Ionophore A23187 in the Development of Irinophore C™" Pharm Res. Apr. 2011;28(4):848-57.
Ramsay E et al. "A novel liposomal irinotecan formulation with significant anti-tumour activity: Use of the divalent cation ionophore A23187 and copper-containing liposomes to improve drug retention" Eur J Pharm Biopharm. Mar. 2008;68(3):607-17.
Ramsay E et al. "Irinophore C: A Liposome Formulation of Irinotecan with Substantially Improved Therapeutic Efficacy against a Panel of Human Xenograft Tumors" Clin Cancer Res. Feb. 15, 2008;14(4):1208-17.

(Continued)

*Primary Examiner* — Janet Epps-Smith

(74) *Attorney, Agent, or Firm* — Pearl Cohen Zedek Latzer Baratz LLP

(57) ABSTRACT

The present invention relates to the use of copper ions to achieve enhanced retention of a therapeutic agent within a liposome. The invention may be employed to more effectively deliver a liposomally encapsulated therapeutic agent to a target site in vitro and in vivo for anti-cancer or other therapy. The liposome may comprise an interior buffer solution containing the therapeutic agent, the solution having a pH less than 6.5 and most preferably approximating pH 3.5. At least some of the copper ions are retained within the interior solution. In a particular embodiment the therapeutic agent may be a chemotherapeutic drug, such as irinotecan. The invention may also comprise an ionophore to facilitate loading of drug into the liposome. In one particular embodiment the combination of the ionophore A23187 and encapsulated divalent copper (Cu2+) resulted in an irinotecan formulation that exhibited surprisingly improved drug retention attributes.

26 Claims, 23 Drawing Sheets

(56) References Cited

OTHER PUBLICATIONS

Ramsay E et al. "Transition Metal-Mediated Liposomal Encapsulation of Irinotecan (CPT-11) Stabilizes the Drug in the Therapeutically Active Lactone Conformation" Pharm Res. Dec. 2006;23(12):2799-808.

Taggar A S et al. "Copper-topotecan complexation mediates drug accumulation into liposomes" J Control Release. Aug. 10, 2006;114(1):78-88.

Tardi P et al. "Coencapsulation of irinotecan and floxuridine into low cholesterol-containing liposomes that coordinate drug release in vivo" Biochim Biophys Acta. Mar. 2007;1768(3):678-87.

International Search Report of corresponding International Application No. PCT/CA2005/001536 dated Jan. 18, 2006.

European Search Report for the corresponding application: EP 05 79 1552 dated Nov. 4, 2010.

Abraham et al. "Characterization of Doxorubicin and Vincristine Coencapsulated within Liposomes through Use of Transition Metal Ion Complexation and pH Gradient" Clin Cancer Res. Jan. 15, 2004;10(2):728-38.

* cited by examiner (▲) 300mM CuSO₄ pH 3.5 + HPTS
(△) 300mM CuSO₄/20mM HEPES/TEA pH 7.5 + HPTS

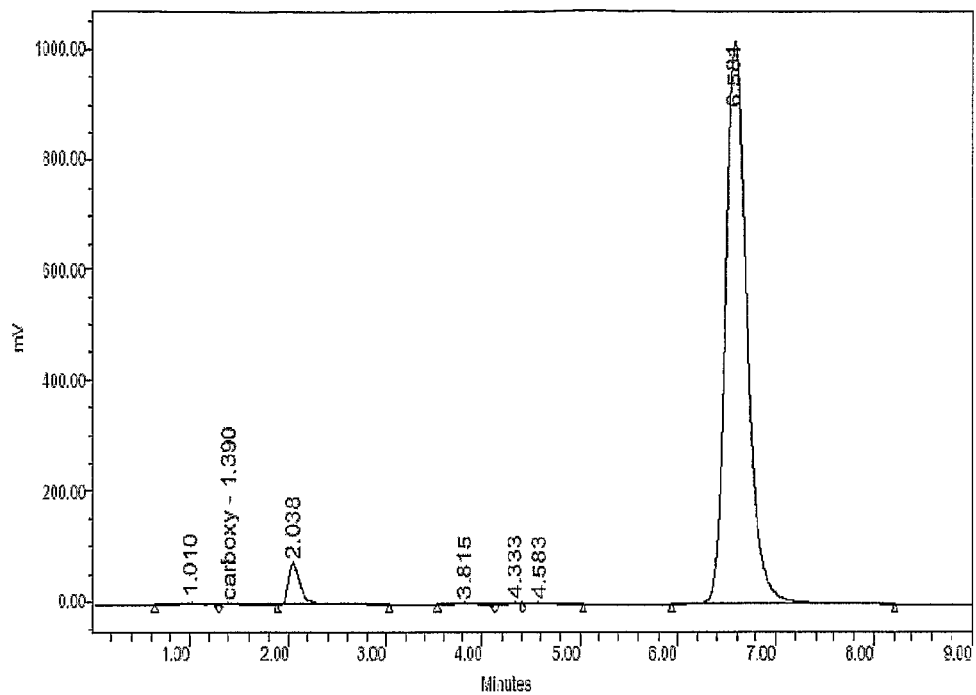
A – Unbuffered CuSO$_4$ (initial pH 3.5)
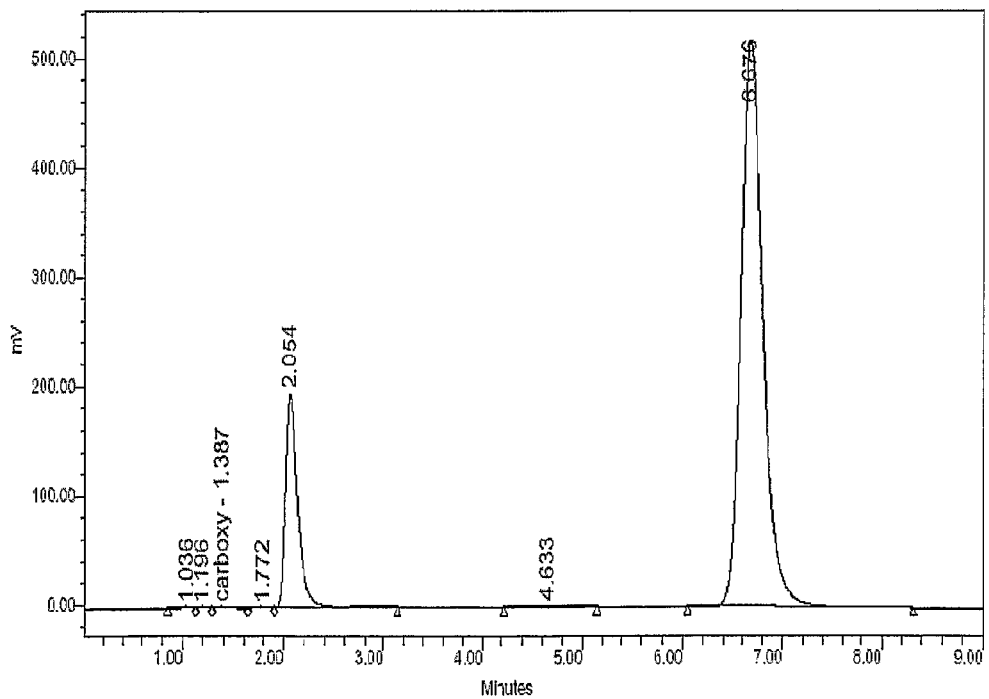
B – CuSO$_4$ buffered pH 7.5
FIGURE 5

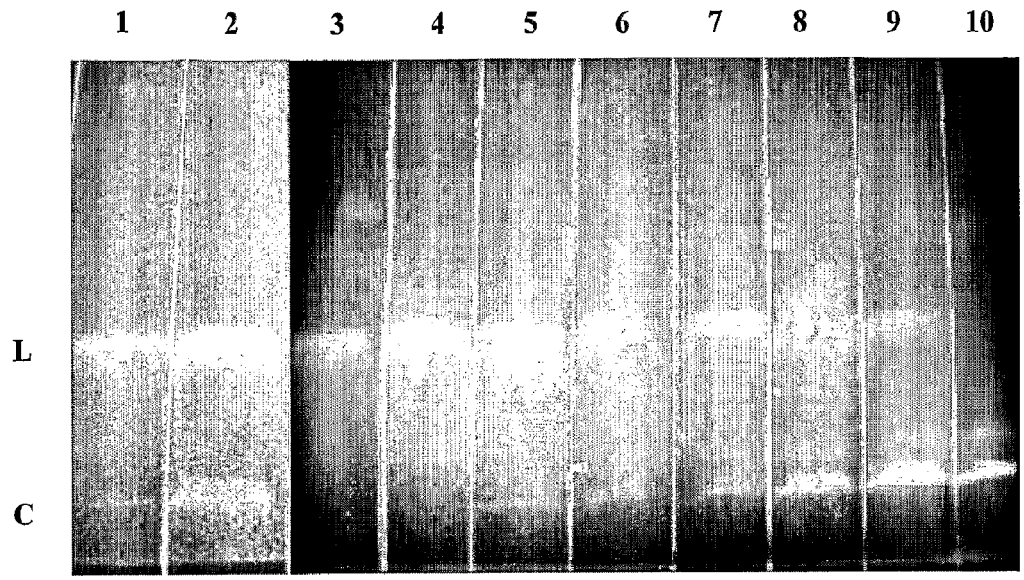

L – lactone
C – carboxy

1 - Unbuffered CuSO₄ (initial pH 3.5)
2 - CuSO₄ buffered pH 7.5
3 – unencapsulated irinotecan control at pH 2.0
4 – unencapsulated irinotecan control at pH 5.5
5 – unencapsulated irinotecan control at pH 6.0
6 – unencapsulated irinotecan control at pH 6.5
7 – unencapsulated irinotecan control at pH 7.0
8 – unencapsulated irinotecan control at pH 7.5
9 – unencapsulated irinotecan control at pH 8.0
10 – unencapsulated irinotecan control at pH 10.0

FIGURE 6

(■) CuSO₄ pH 7.5
(●) CuSO₄ pH 3.5
(▲) MnSO₄ pH 3.5 + A23187
(♦) CuSO₄ pH 3.5 + A23187

(■)  CuSO₄ pH 7.5
(●)  CuSO₄ pH 3.5
(▲)  MnSO₄ pH 3.5 + A23187
(♦)  CuSO₄ pH 3.5 + A23187

(■) CuSO₄ pH 7.5
(●) CuSO₄ pH 3.5
(▲) MnSO₄ pH 3.5 + A23187
(♦) CuSO₄ pH 3.5 + A23187

(■) CuSO₄ pH 7.5
(●) CuSO₄ pH 3.5
(▲) MnSO₄ pH 3.5 + A23187
(♦) CuSO₄ pH 3.5 + A23187

―□― F-CPT-11 (147.7μmol/kg)
―■― F-CPT-11 (73.8μmol/kg)
―▲― L-CPT-11 (73.8μmol/kg) pH7.5
―△― L-CPT-11 (147.7μmol/kg) pH7.5
―▼― L-CPT-11 (73.8μ,mol/kg) pH3.5
―▽― L-CPT-11 (147.7μmol/kg) pH3.5
―◆― L-CPT-11 (73.8μmol/kg) pH3.5 + A23187
―◇― L-CPT-11 (147.7μmol/kg) pH3.5 + A23187
―●― saline

| DRUG | DOSE (µmol/kg) | LIPID DOSE (µmol/kg) | MAX MEAN % BWL | 400% N= | T-C | % GROWTH DELAY | LOG CELL KILL | % CELL KILL |
|---|---|---|---|---|---|---|---|---|
| CPT-11 | 73.8 (50) | NA | 5.7 | 3/6 | 0.3 | 1.2 | 0.02 | 4.5 |
|  | 147.7 (100) |  | 8.5 | 4/6 | 4 | 16.3 | 0.28 | 47.7 |
| Liposomal CPT-11 300mM CuSO4/20mM HEPES/TEA pH 7.5 | 73.8 (50) | 369 | 11.4 | 4/6 | 1.5 | 7.0 | 0.12 | 24.2 |
|  | 147.7 (100) | 738.5 | 19.6 | 4/6 | 5.8 | 26.7 | 0.46 | 65.5 |
| Liposomal CPT-11 300mM CuSO4 pH3.5 | 73.8 (50) | 369 | 12.9 | 4/6 | 3.8 | 17.4 | 0.30 | 50.0 |
|  | 147.7 (100) | 738.5 | 23.8 | 4/6 | 9.5 | 44.2 | 0.76 | 82.7 |
| Liposomal CPT-11 300mM CuSO4 pH3.5 + A23187 | 73.8 (50) | 369 | 15.3 | 5/6 | 7.1 | 33.0 | 0.57 | 73.1 |
|  | 147.7 (100) | 738.5 | toxic |  |  |  |  |  |

FIGURE 18

| Treatment | Irinotecan dose (μmol/kg) | Irinotecan AUC (h • μmol/ml) | Irinotecan MRT (h) | % Growth Delay |
|---|---|---|---|---|
| Unencapsulated irinotecan | 73.8 | <0.1 | <0.01 | 1.2 |
| DSPC/Chol irinotecan (300mM CuSO$_4$/20mM HEPES/TEA pH 7.5 | 73.8 | 22.84 | 4.12 | 7.0 |
| DSPC/Chol irinotecan (unbuffered 300mM CuSO$_4$ pH 3.5) | 73.8 | 27.09 | 5.49 | 17.4 |
| DSPC/Chol irinotecan (unbuffered 300mM MnSO$_4$ + A23187) | 73.8 | 32.44 | 5.41 | ND |
| DSPC/Chol irinotecan (unbuffered 300mM CuSO$_4$ + A23187) | 73.8 | 50.02 | 7.36 | 33.0 |

FIGURE 21

LIPOSOMES WITH IMPROVED DRUG RETENTION FOR TREATMENT OF CANCER

CROSS-REFERENCE TO RELATED APPLICATIONS

This application is a Divisional application of U.S. patent application Ser. No. 11/576,595, filed Jan. 9, 2008, which is a National Phase Application of PCT International Application No. PCT/CA2005/001536, International Filing Date Oct. 6, 2005, claiming priority of U.S. Provisional Application No. 60/615,943, filed Oct. 6, 2004, which are all hereby incorporated by reference in their entirety.

FIELD OF THE INVENTION

This invention relates to a liposome drug loading method and composition that provides superior drug retention, enabling enhanced delivery of therapeutic compounds in vivo.

BACKGROUND OF THE INVENTION

Liposomes are microscopic particles that are made up of one or more lipid bilayers enclosing an internal compartment. Liposomes can be categorized into multilamellar vesicles, multivesicular liposomes, unilamellar vesicles and giant liposomes. Liposomes have been widely used as carriers for a variety of agents such as drugs, cosmetics, diagnostic reagents, and genetic material. Since liposomes consist of non-toxic lipids, they generally have low toxicity and therefore are useful in a variety of pharmaceutical applications. In particular, liposomes are useful for increasing the circulation lifetime of agents that have a short half-life in the bloodstream. Liposome encapsulated drugs often have biodistributions and toxicities which differ greatly from those of free drug. For specific in vivo delivery, the sizes, charges and surface properties of these carriers can be changed by varying the preparation methods and by tailoring the lipid makeup of the carrier. For instance, liposomes may be made to release a drug more quickly by decreasing the acyl chain length of a lipid making up the carrier.

The most efficient method of encapsulating a high drug payload in liposomes is via active loading. This process is mediated by the creation of pH gradients ($\Delta$pH) or metal ion gradients ($\Delta M2+$) across the liposomal membrane. For example, a $\Delta$pH generated by preparing liposomes in citrate buffer pH 4.0 followed by exchange of external buffer with buffered-saline pH 7.5, can promote the liposomal accumulation of weakly basic drugs. The neutral form of the drug passively diffuses across the lipid bilayer and becomes trapped upon protonation in the low pH environment of the liposome interior. This process can result in >98% drug encapsulation and high drug-to-lipid ratios (e.g. vinorelbine). Drug loading via $\Delta M2+$ follows an analogous process, with drug accumulation being driven by metal ion-complexation (e.g. doxorubicin-$Mn2+$). Drug loading efficiencies driven by metal ion-complexation are comparable to those described for $\Delta$pH.

A further active loading procedure uses a combination of an ionophore, such as A23187, and divalent metal ions (M2+). A23187 incorporates into the lipid bilayer and exchanges 1M2+ from the interior liposome buffer for 2H+ from the external buffer, thereby generating and maintaining a $\Delta$pH. A23187 and an internal $Mn2+$ buffer have been used previously to efficiently encapsulate vincristine, ciprofloxacin, topotecan and irinotecan. The role of $Mn2+$ in this system is believed to be an 'inert' facilitator for the creation of a $\Delta$pH. Indeed, exchanging the internal $Mn2+$-based buffer with a $Cu2+$-based buffer does not result in any differences in the kinetics of anticancer drug loading.

The present invention relates to the use of divalent copper ions ($Cu2+$) to significantly enhance intra-liposomal drug retention attributes and hence in vivo therapeutic effects. For example, a $Cu2+$/A23187 liposomal irinotecan formulation described herein demonstrated significantly improved efficacy against murine xenograft models of colorectal cancer when compared to the $Mn2+$/A23187 equivalent. The Applicant's loading procedure combines high encapsulation efficiencies (>98%), high drug-to-lipid ratios and enhanced drug retention. It is notable that existing inventions describe the use of transmembrane pH gradients, defining the utility of ionophores to generate a transmembrane pH gradients, or alternatively disclose the use of transition metals, such as $Mn2+$ or $Cu2+$, in the presence of a neutral environment and in the absence of a transmembrane pH gradient (Fenske et al., U.S. Pat. No. 5,837,282; Tardi et al., US 20030091621). The prior art does not teach methods and compositions that rely on divalent copper ions ($Cu2+$) in a low pH environment, and it was not anticipated that such compositions would result in improved drug retention attributes.

Liposomes containing metal ions encapsulated in the interior of the vesicle have previously be used in diagnostic applications. For example, liposomes have been used for delivery of contrast agents with the goal of accumulating a contrast agent at a desired site within the body of a subject. In the latter application, liposomes have mainly been used for delivery of diagnostic radionucleotides and paramagnetic metal ions in gamma and magnetic resonance imaging, respectively. However, liposomally encapsulated metal ions in these applications are not employed for drug retention purposes.

Camptothecins are a class of anticancer drugs that inhibit the nuclear enzyme, topoisomerase I (topo I). Topo I facilitates DNA replication during the S phase of the cell cycle by inducing transient single strand breaks in the DNA double-helix. The complex formed between DNA and topo I is referred to as the 'cleavable complex'. Camptothecins induce caspase-mediated cellular apoptosis by stabilising this cleavable complex. Camptothecins, such as irinotecan, possess a lactone ring. This lactone ring is crucial for cytotoxic activity. Liposome formulations of camptothecins are an attractive option based on the potential for these carrier systems to maintain the drug in an environment that favours the active closed ring lactone form. An equilibrium exists between the closed lactone ring form of camptothecins and an inactive open-ring carboxylic acid form (FIG. 1). This equilibrium is influenced by pH. At acidic pH, equilibrium is driven towards the closed lactone ring. At neutral or alkaline pH (e.g. physiological conditions), equilibrium favours the inactive open-ring form.

The need has arisen for improved liposomal formulations which both enhance retention of encapsulated drugs and also preferably maintain the drugs in their active form for improved delivery and efficacy at a target site.

SUMMARY OF THE INVENTION

In one embodiment the invention relates to a composition comprising a liposome encapsulating a therapeutic agent, wherein the therapeutic agent is loaded into the liposome in the presence of intra-liposomal copper ions, and wherein the copper ions enhance the retention of the therapeutic agent within the liposome. The liposome may comprise an interior buffer solution containing the therapeutic agent, the solution having a pH less than 6.5 and most preferably approximating pH 3.5. At least some of the copper ions are retained within the interior solution. In a particular embodiment the therapeutic agent may be an anti-cancer drug, such as irinotecan or vinorelbine.

The invention also relates to a method of enhancing the retention of a therapeutic agent within liposomes comprising the steps of (a) providing within an interior of the liposomes an intra-liposomal solution comprising copper ions; (b) maintaining the pH of the intra-liposomal solution below 6.5; (c) providing a therapeutic agent in the external solution, wherein the therapeutic agent diffuses into the interior and is encapsulated within the liposomes, and wherein the presence of the copper ions enhances the retention of the therapeutic agent therein.

BRIEF DESCRIPTION OF THE DRAWINGS

In drawings which describe embodiments of the invention but which should not be construed as restricting the spirit or scope of the invention in any way.

FIG. 5 are HPLC plots demonstrating that irinotecan exists predominately as its lactone form irrespective of whether the encapsulated CuSO4 solution was unbuffered or buffered to pH 7.5

FIG. 6 shows the results of TLC analysis demonstrating that irinotecan exists predominately as its lactone form irrespective of whether the encapsulated CuSO4 solution was unbuffered or buffered to pH 7.5

FIG. 18 is a table summarizing data derived from analysis of a single dose of CPT-11 (free or DSPC/Chol encapsulated (55:45 mol %) used to treat SCID/Rag2M mice with established tumours derived following s.c. injection of LSI80 human adenocarcinoma cells.

FIG. 21 is a table summarizing data derived from analysis of a single dose of (73.8 µmol/kg; 50 mg/kg) of unencapsulated irinotecan or liposomal irinotecan (DPSC/Chol 55:45 mol %; irinotecan loading mediated by different technologies) administered to Rag-2M mice. The pharmacokinetic parameters of the different irinotecan treatments were determined and related to their therapeutic effectiveness against established s.c. LSI80 tumours (human colorectal carcinoma xenograft).

DETAILED DESCRIPTION OF THE INVENTION

Throughout the following description specific details are set forth in order to provide a more thorough understanding of the invention. However, the invention may be practiced without these particulars. In other instances, well known elements have not been shown or described in detail to avoid unnecessarily obscuring the present invention. Accordingly, the specification and drawings are to be regarded in an illustrative, rather than a restrictive, sense.

The Applicant's invention provides new methods and compositions to improve the effectiveness of liposomal drug delivery. The invention is based on the discovery that the drug retention properties of a liposome employing a divalent metal cation for drug loading purposes is surprisingly dependent on the metal employed. By selecting the optimal metal, namely divalent copper, retention properties can be tailored to achieve a desired release of a selected agent from a liposome.

As described above, various methods are known in the prior art for actively loading drugs into liposomes. The present invention relies on a pH gradient established across the liposomal membrane for moving a therapeutic agent from an external solution into the interior of the liposomes. The pH gradient may be established and maintained in various manners as will be appreciated by a person skilled in the art. In one embodiment of the invention, an intra-liposomal solution is maintained at a pH below about 6.5. In particular embodiments the intra-liposomal pH is maintained within the range of about 2 and 5, most preferably about pH 3.5. This may be achieved, for example, by providing a buffer in the intra-liposomal solution or by providing an ionophore for facilitating exchange of ions between the interior solution and the external solution. The ionophore may be of any chemical class enabling the exchange of the internal metal ion for two external protons. In one preferred embodiment it consists of A23187. In an alternative embodiment the ionophore may consist of ionomycin, or X-537A.

Figure 19:
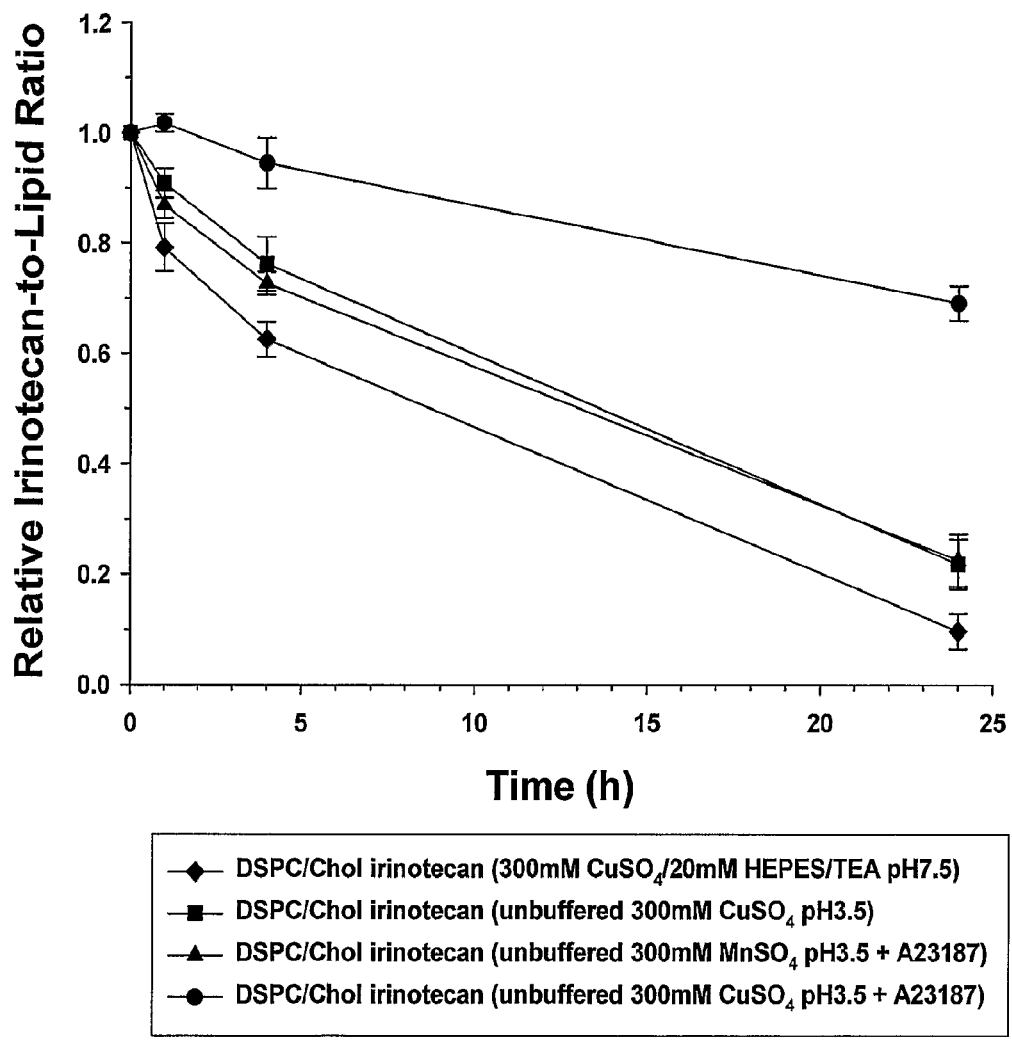
FIG. 19 is graph showing relative irinotecan-to-lipid ratios in the plasma following a single i.v. bolus injection (73.8 µmol/kg; 50 mg/kg) administered to Rag-2M mice. The formulations consisted of the same liposome composition (DSPC/Chol 55:45 mol %) with different internal solutions as indicated in the legend. The formulation prepared by the $Cu^{2+}$/A23187 drug loading technology demonstrates significantly better plasma drug retention as demonstrated by the higher relative irinotecan-to-lipid ratio after 24 hours.
Figure 20:
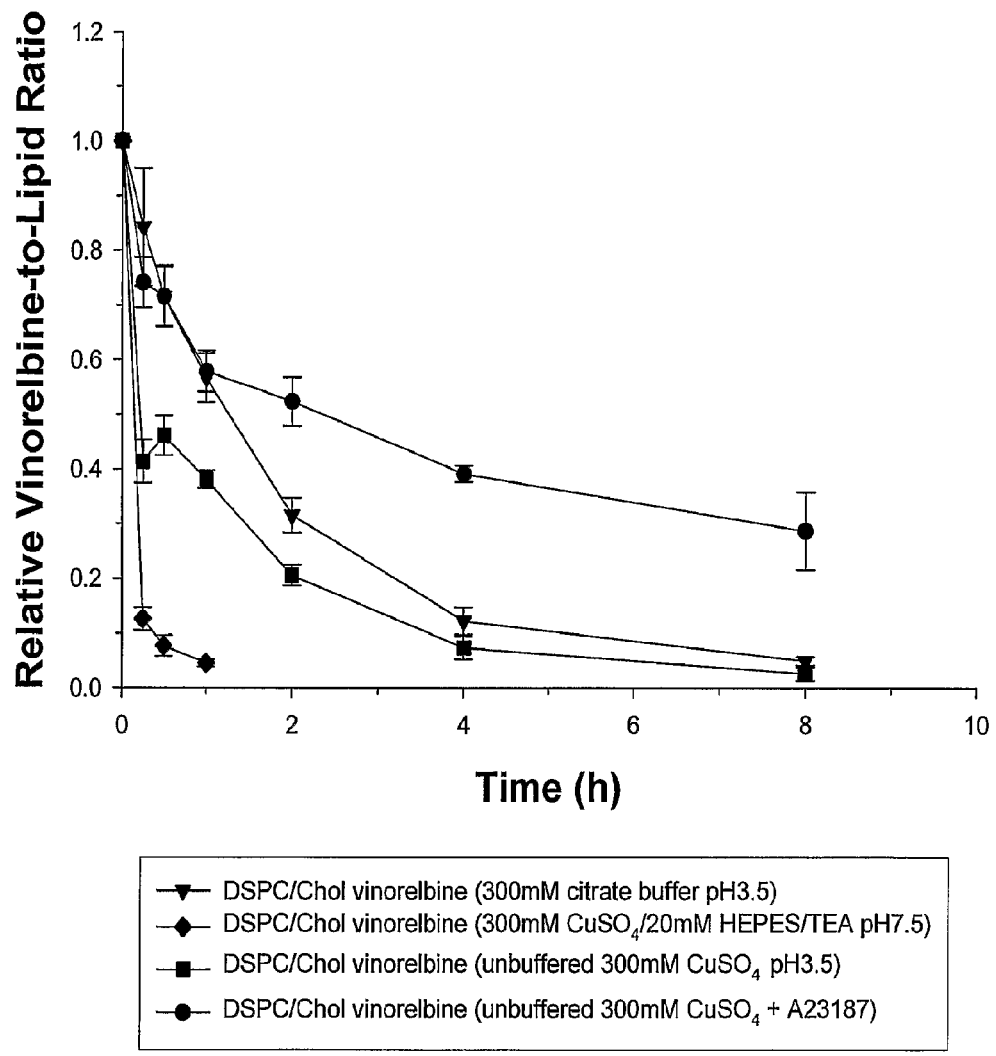
FIG. 20 is a graph showing relative vinorelbine-to-lipid ratios in the plasma following a single i.v. bolus injection (18.5 µmol/kg; 20 mg/kg) administered to Rag-2M mice. The formulations consisted of the same liposome composition (DSPC/Chol 55:45 mol %) with different internal solutions as indicated in the legend. The formulation prepared by the $Cu^{2+}$/A23187 drug loading technology demonstrates significantly better plasma drug retention as demonstrated by the higher relative vinorelbine-to-lipid ratio after 8 hours.

Irrespective of how the therapeutic agent is actively loaded into the liposomes (i.e. how the pH gradient is established), the present invention relates to the use of divalent copper ions within the intra-liposomal solution to enhance retention of the encapsulated therapeutic agent. The exact mechanism by which the copper ions function has not yet been elucidated. For example, the copper may bind to the therapeutic agent and/or it may modify the permeability of the liposome membrane. Even in the case where the ionophore facilitates exchange of copper ions in divalent form from the interior of the liposome to the external solution, at least some copper ions remain retained within the liposomes. As described further below, the presence of copper in the intra-liposomal solution may significantly enhance the retention and therapeutic efficacy of the agent in vivo. As will be apparent to a person skilled in the art, the retention of the therapeutic agent is "enhanced" in comparison to similar liposomal formulations which lack copper. As described in detail below, enhanced drug retention may be determined by in vivo tests, such as plasma drug retention (FIGS. 19 and 20).

The therapeutic agents may be of any class which has improved retention in liposomes when loaded in the presence of intra-liposomal copper. In one preferred embodiment the compound may be any weakly basic compound. In another preferred embodiment the therapeutic compound may be a topoisomerase inhibitor, preferably a camptothecin or an analogue thereof, most preferably irinotecan (CPT-11). In an alternative embodiment, the therapeutic compound may be a compound that binds to tubulin preferably from the class of vinca alkaloids. Vinblastine and vincristine are alkaloids found in the Madagascar periwinkle, *Catharanthus roseus* (formerly classified as *Vinca rosea*, which led to these compounds becoming called Vinca alkaloids). They and vindesine and vinorelbine, semisynthetic derivatives of vinblastine, all work by inhibiting mitosis (cell division) in metaphase. The preferred vinca alkaloid for this invention is vinorelbine.

In another alternative embodiment, this invention provides the use of small molecules (chemical compounds), proteins, antibodies or peptides or any new or known composition of matter or pharmaceutically acceptable salt thereof, to be encapsulated into a liposome in conjunction with a divalent copper ion to achieve superior retention properties.

The composition of the liposome consists of lipids 1,2-distearoyl-sn-glycero-3-phosphocholine (DSPC)/Cholesterol (55:45 mol %) and the ratios of the lipids may vary according to embodiments visualized by persons skilled in the art of liposome preparation. In an alternative embodiment the liposome may consist of lipids including phosphoglycerides and sphingolipids, representative examples of which include phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine or dilinoleoylphosphatidylcholine. Other compounds lacking in phosphorus, such as sphingolipid and glycosphingolipid families are also contemplated. Additionally, the amphipathic lipids described above may be mixed with other lipids including triacyglycerols and sterols.

A further modification contemplated within the scope of this invention, is inclusion of a targeting antibody on the surface of the liposome to enable specific localization of the liposome to areas of disease; for example metastatic cancer cells which have spread to other sites in the body.

Numerous diseases and conditions can be contemplated which would benefit from liposomes which increase drug retention, enabling therapeutic drug interventions with superior ADMET (absorption, distribution, metabolism, excretion and toxicity) properties. Such diseases would be including but not limited to the treatment of cancer.

Preferably the pharmaceutical liposomal compositions are administered parentally, i.e. intraarticularly, intravenously, subcutaneously, or intramuscularly. In other embodiments, the pharmaceutical preparation may be administered topically.

In one particular embodiment of the invention, encapsulated irinotecan with copper in the presence of A23187 ionophore exhibited unexpectedly superior retention of the irinotecan within the liposome in vivo and in addition exhibited enhanced potency compared to irinotecan prepared with copper-mediated loading in the absence of A23187 ionophore. In addition, the encapsulated irinotecan exists predominately in the clinically active lactone form.

The following examples will further illustrate the invention in greater detail although it will be appreciated that the invention is not limited to the specific examples.

Example 1.0

1.1 Materials and Methods 1.1.1 Liposome Formation

DSPC/Chol (55:45 mol %) large unilamellar vesicles (LUVs) were prepared by the extrusion method. Briefly, lipids were dissolved in chloroform at the required molar ratio, labelled with the non-exchangeable, non-metabolizable lipid marker, 3H-CHE and dried to a thin film under a stream of nitrogen gas. Subsequently, the lipid was placed in a high vacuum for 3 hours to remove any residual solvent. The lipid films were then hydrated at 65° C. by mixing with the appropriate buffer (300 mM CuS04, 300 mM C0S04, 300 mM ZnS04 and 300 mM MnS04). The mixture was subjected to five cycles of freeze-and-thaw (5 minutes each, freezing in liquid nitrogen and thawing at 65° C.). The formed multilamellar vesicles (MLV's) were extruded 10 times through stacked polycarbonate filters of 0.1 μm pore size at 65° C. (Extruder, Northern lipids). The resultant LUVs typically possessed mean vesicular diameters in the range 110 nm±30 nm. The LUVs' external buffer was exchanged with SHE pH 7.5 (300 mM sucrose, 20 mM HEPES, 15 mM EDTA) using sephadex G-50 size exclusion chromatography.

1.1.2 Metal Ion Gradient Formation

Extruded DSPC/Chol liposomes were prepared in unbuffered sulfate salt solutions of copper, zinc, manganese, or cobalt. The external buffers were exchanged with sucrose/HEPES/EDTA (SHE) buffer pH 7.5 to create a metal ion gradient. The efficiency of irinotecan loading (drug-to-lipid ratio of 0.2 mol:mol) at 50° C. was determined over 60 min. The role of internal liposome pH on the efficiency of drug loading was assessed using internal buffers comprising (CuS04/HEPES/TEA pH 7.5), or unbuffered CuS04+

A23187 ionophore. When using A23187, Cu2+ ions from the liposome interior are exchanged for two protons from the external buffer thus maintaining a low internal pH. The membrane-impermeant pH-sensitive fluorescent probe, HPTS was used to investigate any changes in internal pH following copper-mediated irinotecan encapsulation (initial internal pH of 7.5 or 3.5—no ionophore). HPLC and TLC methods were used to assess the carboxy and lactone contents of liposomal irinotecan.

1.1.3 Irinotecan Loading

Drug was incubated with lipid at 50° C. at a drug:lipid ratio=0.2:1 (mol:mol). Uptake of the drug was determined at various timepoints by sampling aliquots and separating encapsulated drug from unencapsulated drug using 1 ml sephadex G-50 spin columns equilibrated with the appropriate buffer (680 g×3 min). The excluded fractions, containing the liposomes, were analyzed in order to determine drugdipid ratios. Lipid concentrations were measured using liquid scintillation counting. Irinotecan concentrations were determined by measuring absorbance at 370 nm.

1.2 Results 1.2.1 Irinotecan Loading Efficiencies

Extruded DSPC/Chol liposomes were prepared in unbuffered sulfate salt solutions of copper, zinc, manganese, or cobalt. The external buffers were exchanged with sucrose/HEPES/EDTA (SHE) buffer pH 7.5 to create a metal ion gradient. The efficiency of irinotecan loading (drug-to-lipid ratio of 0.2 mol:mol) at 50° C. was determined over 60 min. The role of internal liposome pH on the efficiency of drug loading was assessed using internal buffers comprising (CuSO4/HEPES/TEA pH 7.5), or unbuffered CuSO4+ A23187 ionophore. When using A23187, Cu2+ ions from the liposome interior are exchanged for two protons from the external buffer thus maintaining a low internal pH. The membrane-impermeant pH-sensitive fluorescent probe, HPTS was used to investigate any changes in internal pH following copper-mediated irinotecan encapsulation (initial internal pH of 7.5 or 3.5—no ionophore). HPLC and TLC methods were used to assess the carboxy and lactone contents of liposomal irinotecan.

Irinotecan loading efficiencies were >90% using liposomes with encapsulated unbuffered solutions of CuSO4 and ZnSO4. The inclusion of A23187 ionophore, to maintain a low internal pH, did not influence the copper-mediated loading behaviour. When the internal and external buffers were adjusted to pH 7.5 (internal buffer—CuSO4/HEPES/TEA pH 7.5), irinotecan loading was again found to be >90%. HPTS measurements suggest that the internal pH increases following loading via unbuffered CuSO4. HPLC and TLC indicate that encapsulated irinotecan exists predominately as the lactone form (FIG. 5 and FIG. 6) regardless of the initial internal pH of the transition metal solution.

1.2.2 Active Drug Loading of DSPC/Chol Liposomes with Irinotecan

Figure 1:
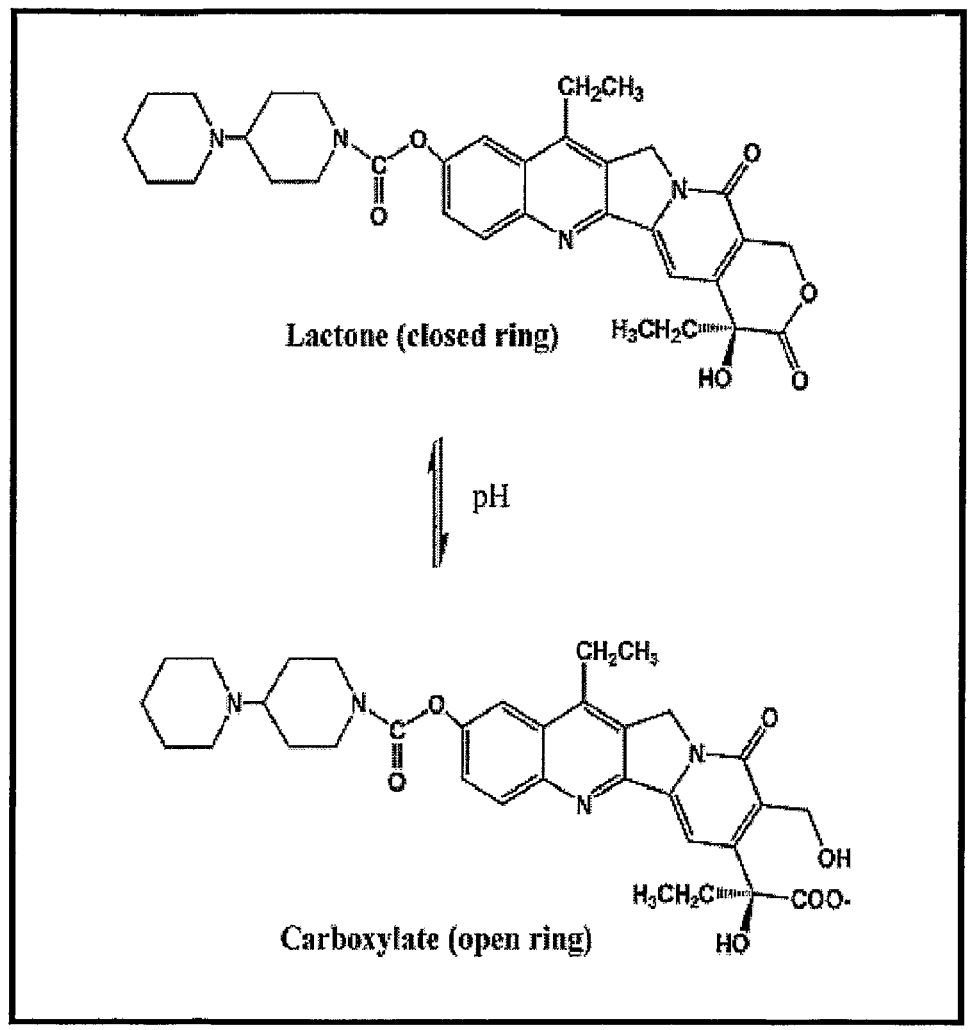
FIG. 1 is a chemical scheme showing a dynamic equilibrium, influenced by pH, which exists between the active closed lactone ring form and inactive open-ring carboxy form of irinotecan.
Figure 2:
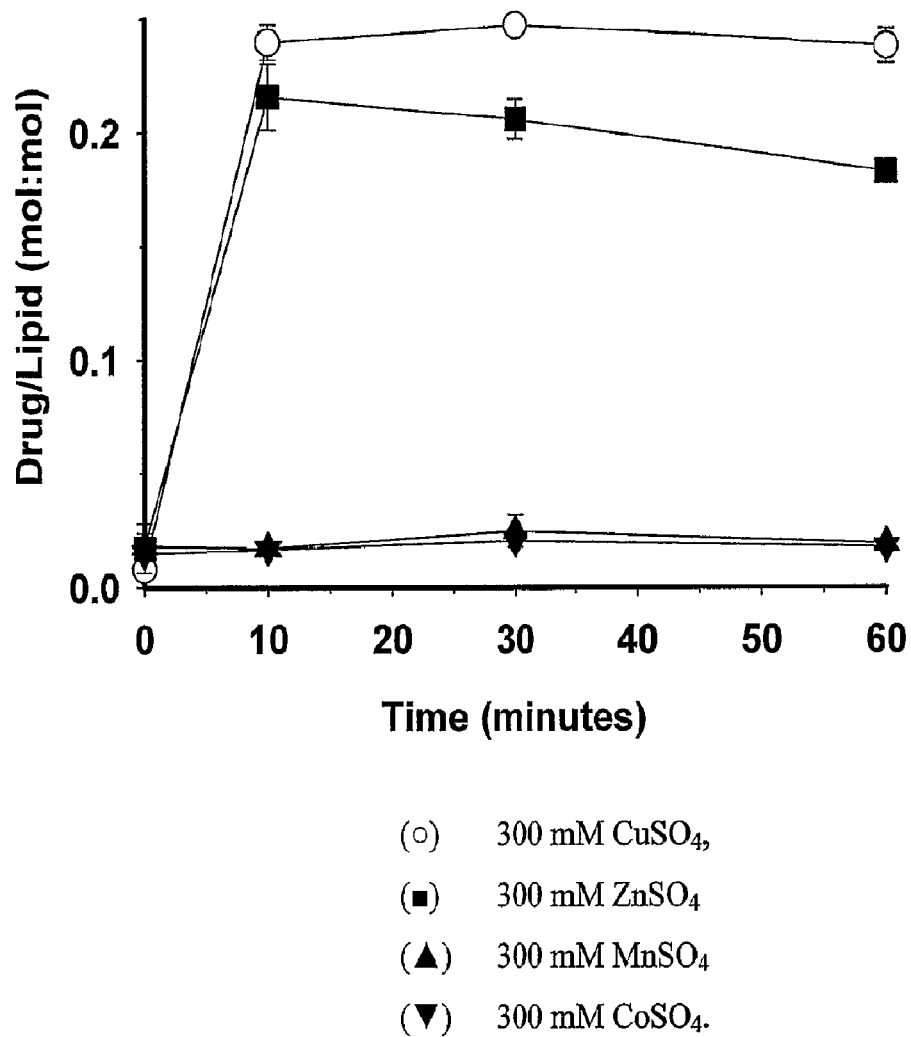
FIG. 2 is a graph showing irinotecan loading efficiencies (drug/lipid ratios) >90% using liposomes with encapsulated unbuffered solutions of CuSO4 or ZnSO4.

Drug was incubated with lipid at 500 C at a drugrlipid ratio=0.2:1 (mol:mol). Uptake of the drug was determined at various timepoints by sampling aliquots and separating encapsulated drug from unencapsulated drug using 1 ml sephadex G-50 spin columns equilibrated with the appropriate buffer (680 g×3 min). The excluded fractions, containing the liposomes, were analyzed in order to determine drug:lipid ratios. Lipid concentrations were measured using liquid scintillation counting. Irinotecan concentrations were determined by measuring absorbance at 370 nm (FIG. 2).

1.2.3 Liposome and Ionophore Preparation

DSPC/Chol (55:45 mol %) large unilamellar vesicles (LUVs) were prepared as described above. The encapsulated buffers in this instance comprised 300 mM CuSO4 (unbuffered), 300 mM CuSO4/20 mM HEPES/220 mM TEA pH 7.5, or 300 n1M CuSO4+A23187 ionophore. The ionophore is incorporated into the liposomal membrane, immediately prior to irinotecan loading, by incubating at 500 C for 10 min. The presence of A23187 facilitates the outward movement of 1×Cu2+ from the liposome interior in exchange for the inward movement of 2×H+ from the exterior buffer. Resultantly, the interior of the liposome is maintained at low pH.

Figure 3:
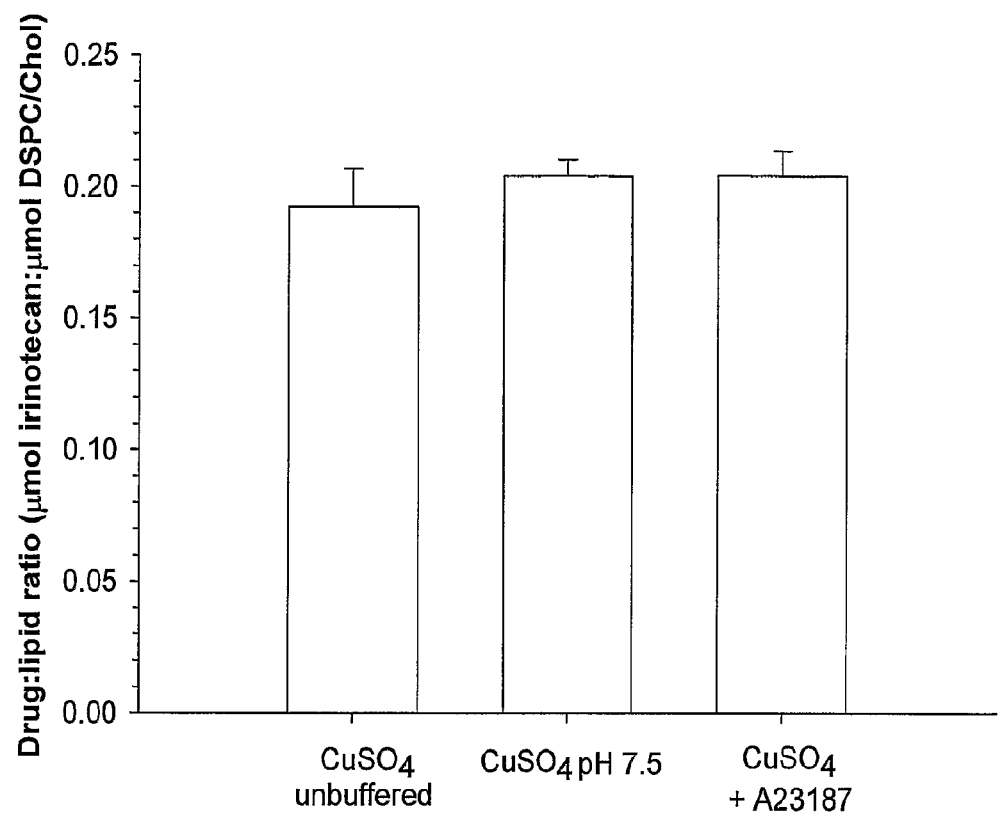
FIG. 3 is a graph showing irinotecan loading efficiencies (drug/lipid ratios) >90% using liposomes with encapsulated buffered CuSO4 pH 7.5 or unbuffered CuSO4+A23187 ionophore (which maintains low pH environment).

1.2.4 Active Drug Loading of DSPC/Chol Liposomes with Irinotecan:

Liposomes were loaded with irinotecan as described above. Irinotecan loading efficiencies remained >90% using liposomes with encapsulated buffered CuSO4 pH 7.5 or unbuffered CuSO4+A23187 ionophore (which maintains low pH environment) as shown in FIG. 3.

1.2.5 Determination of Liposome Internal pH Following Drug Loading

DSPC/Chol (55:45 mol %) liposomes were prepared as previously described. The liposomes were formulated with the following internal buffers, both in the presence or absence of the fluorescent dye, HPTS (12.5 mM): 300 mM CuSO4 unbuffered, 300 mM CuSO4/20 mM HEPES/220 mM TEA pH 7.5, 300 mM citrate pH 3.5 and 20 mM HEPES pH 7.5 Following extrusion the external buffer was exchanged with SHE pH 7.5 using column chromatography as previously described.

Irinotecan was actively loaded into DSPC/Chol liposomes formulated with the internal buffers 300 mM CuSO4 pH 3.5 HPTS and 300 mM CuSO4/20 mM HEPES/TEA pH 7.5 HPTS. Loading conditions were as previously described and the presence of HPTS did not impair the efficiency of irinotecan loading.

HPTS detection was performed using a LS-50B Luminescence Spectrometer (Perkin-Elmer). Liposome solutions were diluted in HBS pH 7.5 to a final lipid concentration of 0.5 mM in order to eliminate lipid-induced interference. The anionic fluorophore HPTS is water-soluble and membrane-impermeant and therefore, can be trapped in the internal compartment of the liposome. The excitation properties of HPTS are dependent on pH such that under acidic conditions the dye has an excitation maximum at 405 nm whereas, increasing pH results in a diminished fluorescence intensity at 405 nm and an increasing intensity at 450 nm. This is exemplified by the scan shown in FIG. 4A which, represents HPTS fluorescent emission at 510 nm following excitation at 350-490 nm for 2 control DSPC/Chol liposome formulations. When the internal buffer is citrate at pH 3.5, HPTS excitation is at a maximum at 405 nm. In contrast, an internal buffer of HEPES pH 7.5 results in a diminished signal at 405 nm and the emergence of significant excitation at 450 nm. The presence of Cu significantly quenches the HPTS signal to approximately 20% of that seen in comparable conditions in the absence of copper (FIG. 4B).

Figure 4A:
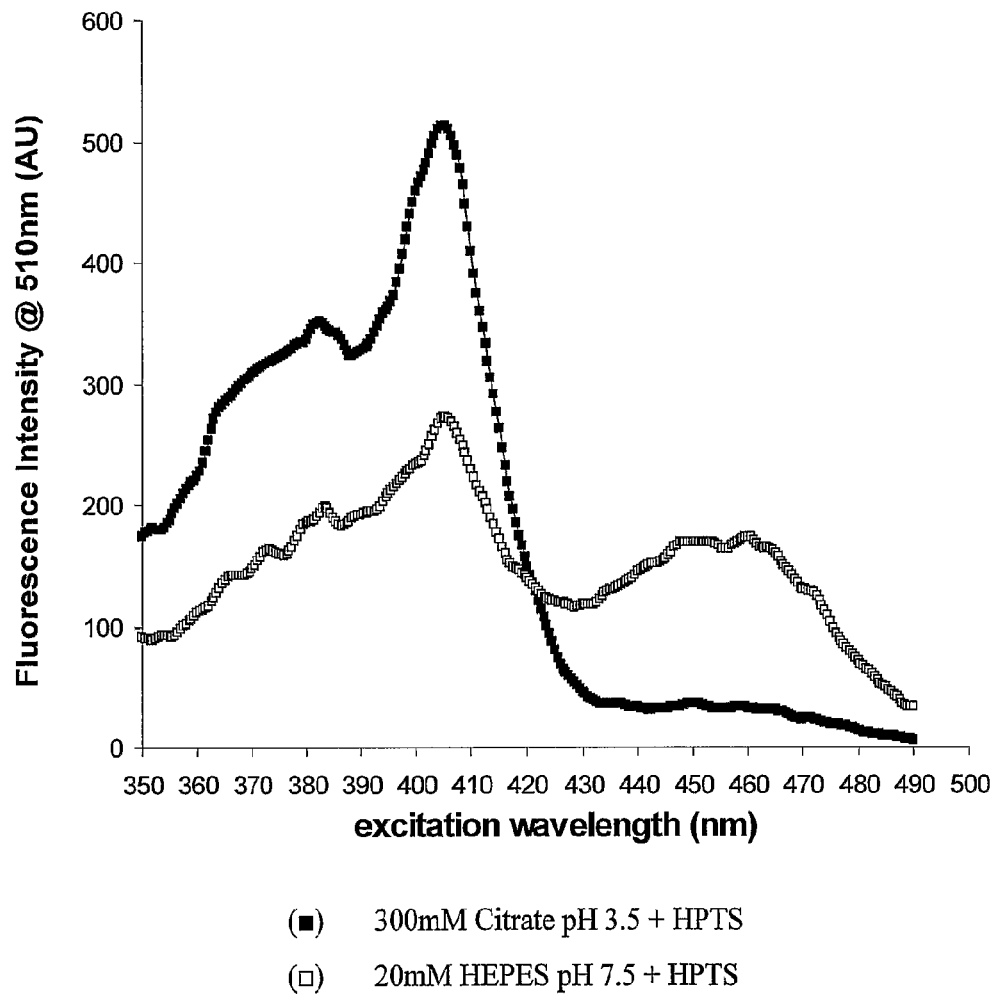
FIG. 4 (A)-(C) are excitation scans showing liposome internal pH following loading of the drug irinotecan. The pH sensitive fluorescent probe, HPTS, suggests that the internal pH of liposomes with encapsulated unbuffered CuSO4 increases following active loading of irinotecan.

One aim of this experiment was to elucidate any internal pH changes following loading of irinotecan into DSPC/Chol liposomes. FIG. 4C represents the excitation scan of the same Cu-containing liposomes described in FIG. 4B with the exception that irinotecan has been actively loaded under the conditions previously described. The increased excitation intensities observed for <400 nm is an artefact of irinotecan loading. Irinotecan is a fluorescently active compound with an excitation wavelength of 368 nm and an emission wavelength of 423 nm. The main point of interest from this excitation scan is the emergence of a significant signal centred around 450 nm for the liposome formulation comprising the unbuffered CuSO4 (pH ~3.5). As we observed from the previous scans there is no significant signal at this wavelength for our control liposome formulation at pH 3.5 (FIG. 4A, FIG. 4B).

Figure 4B:
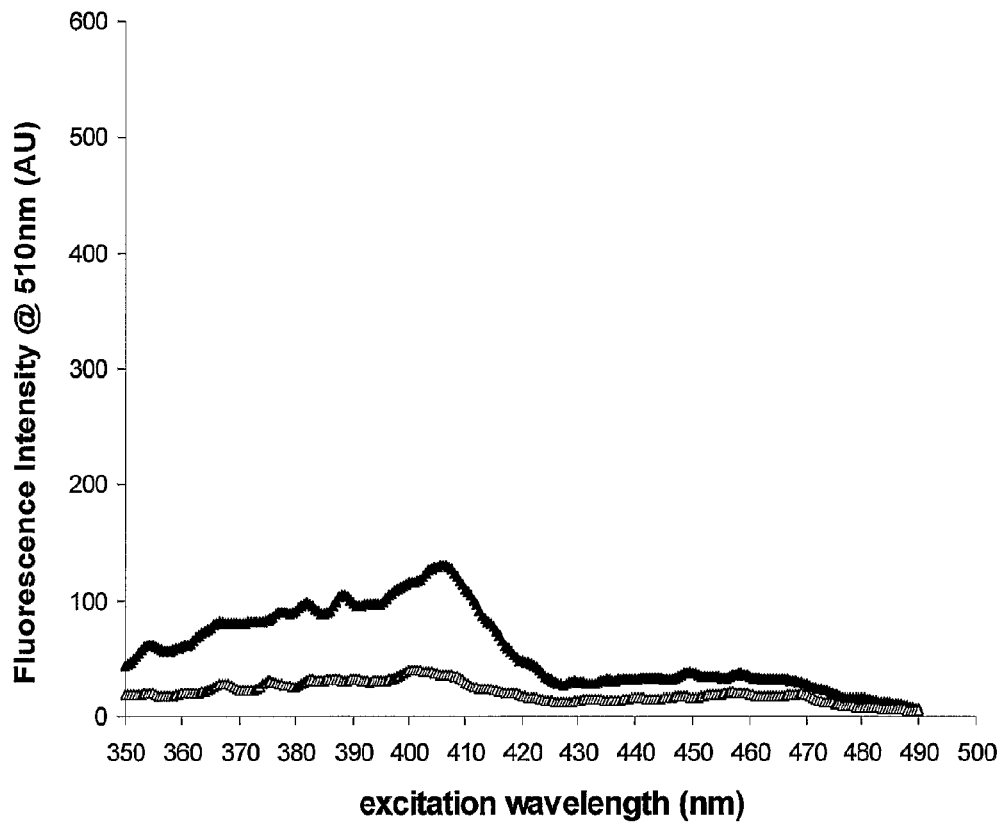
Figure 4C:
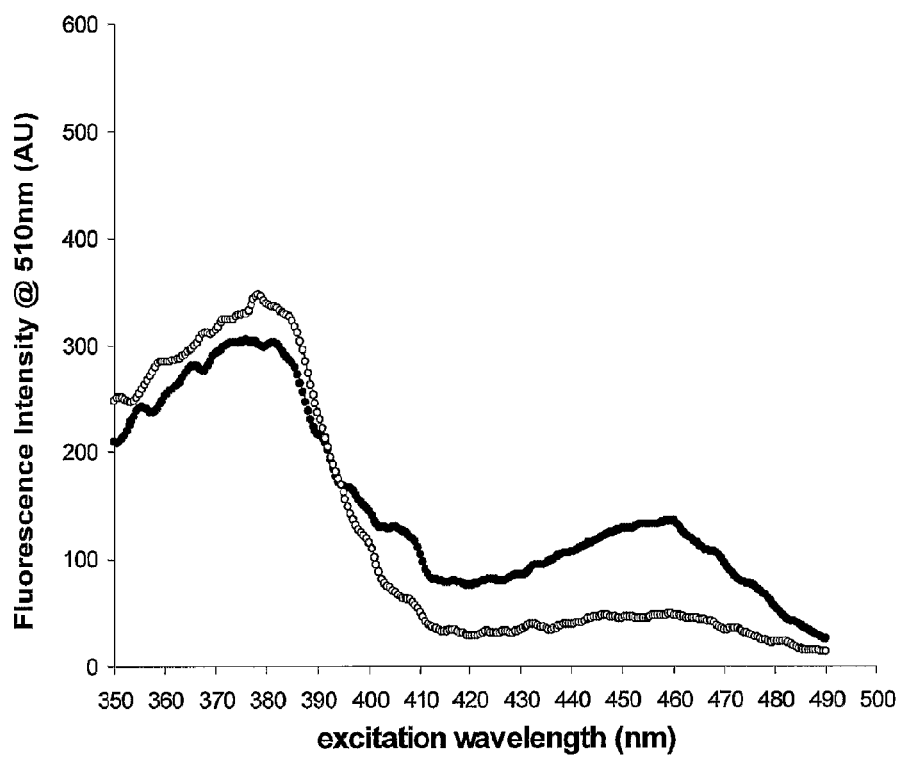
Figure 7:
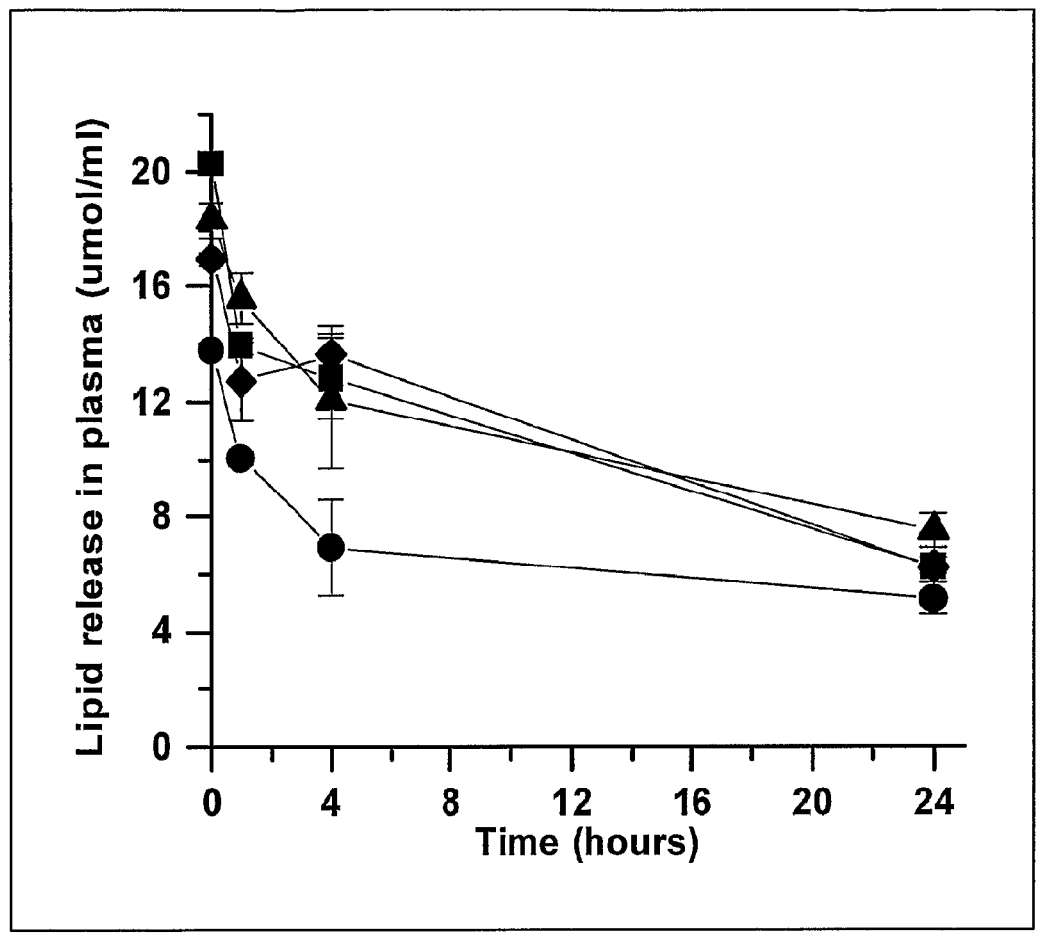
FIG. 7 is a graph showing lipid release of various liposomal formulations in plasma over time.
Figure 8:
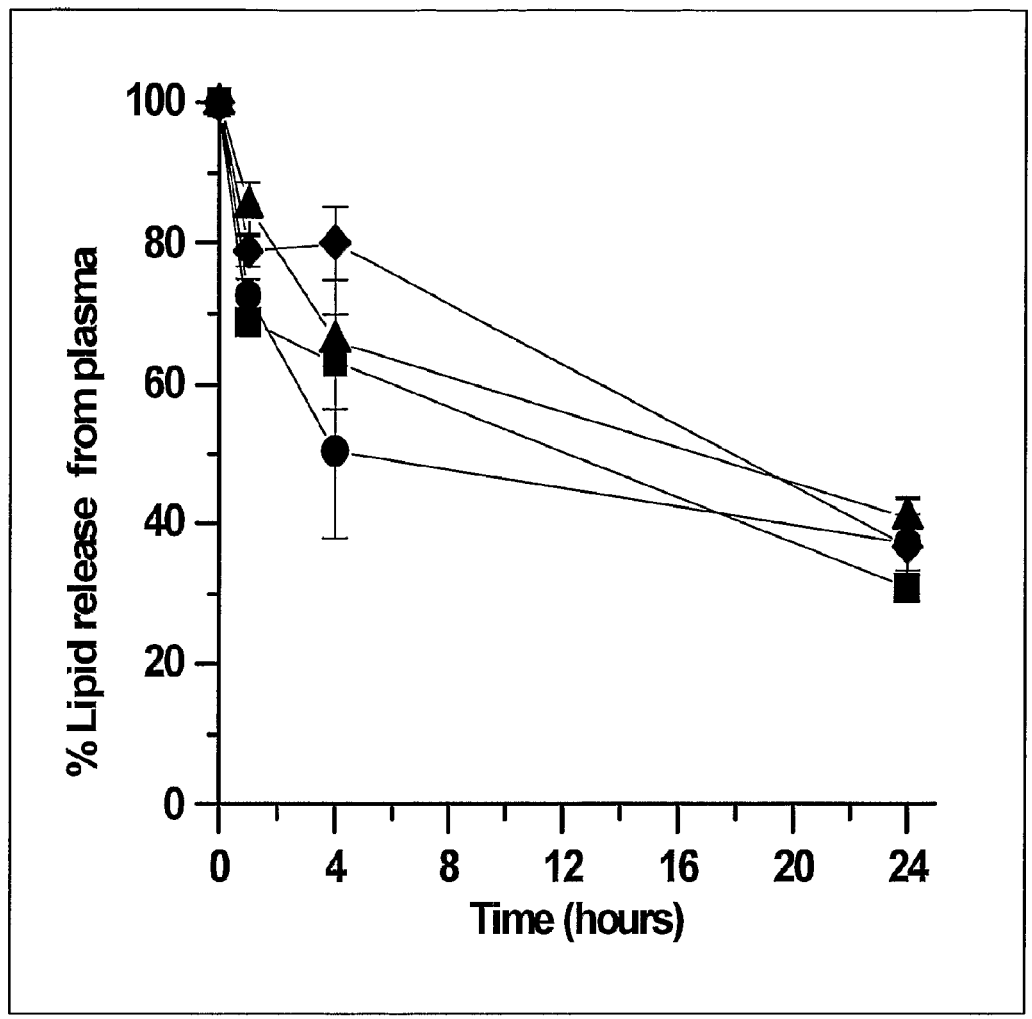
FIG. 8 is a graph showing percentage lipid release of various liposomal formulations in plasma over time.
Figure 9:
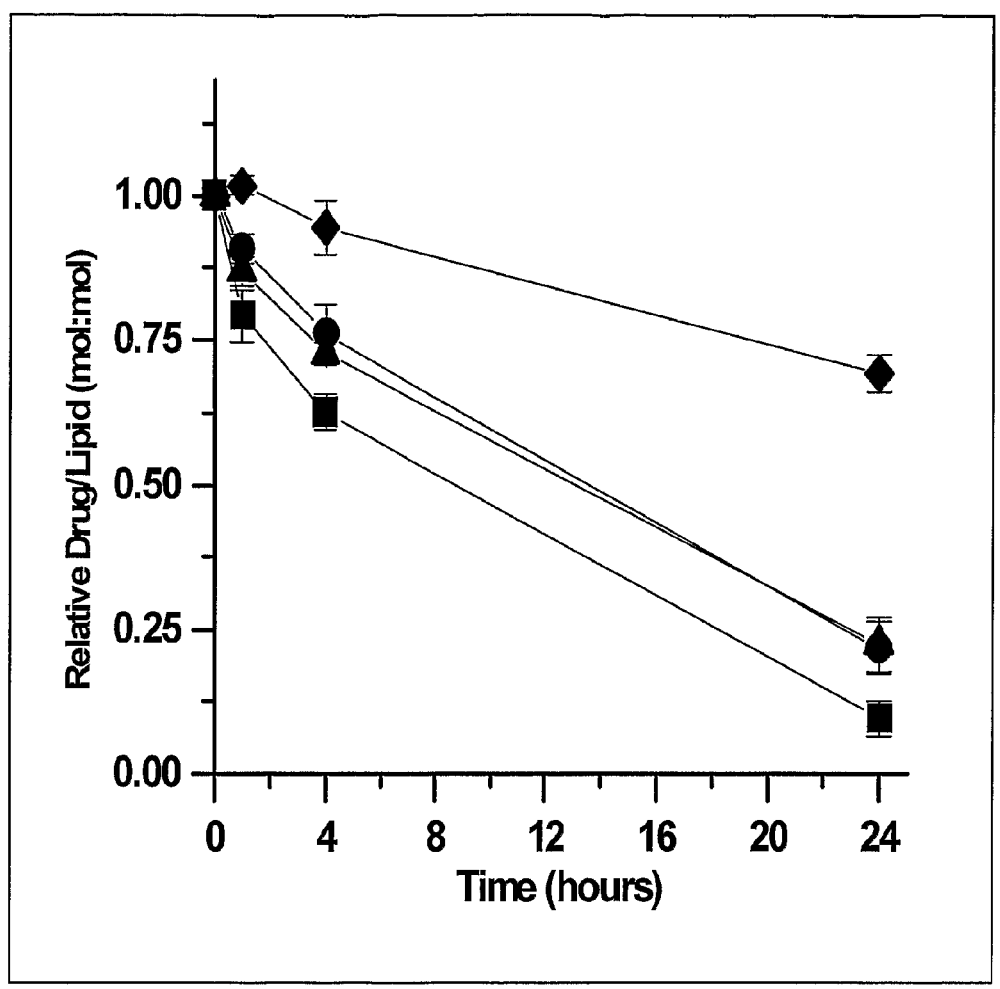
FIG. 9 is a graph showing relative drug:lipid ratios over time.
Figure 10:
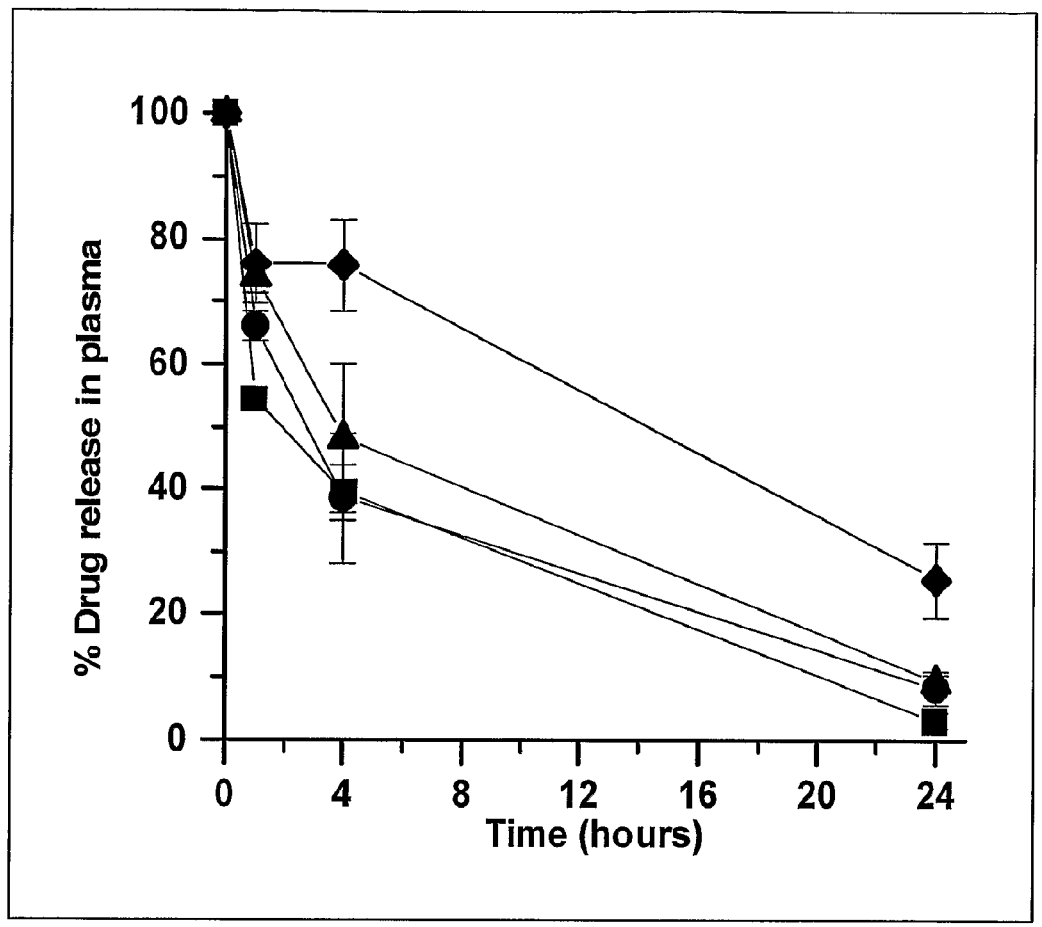
FIG. 10 is a graph showing percentage drug release in plasma over time.
Figure 11:
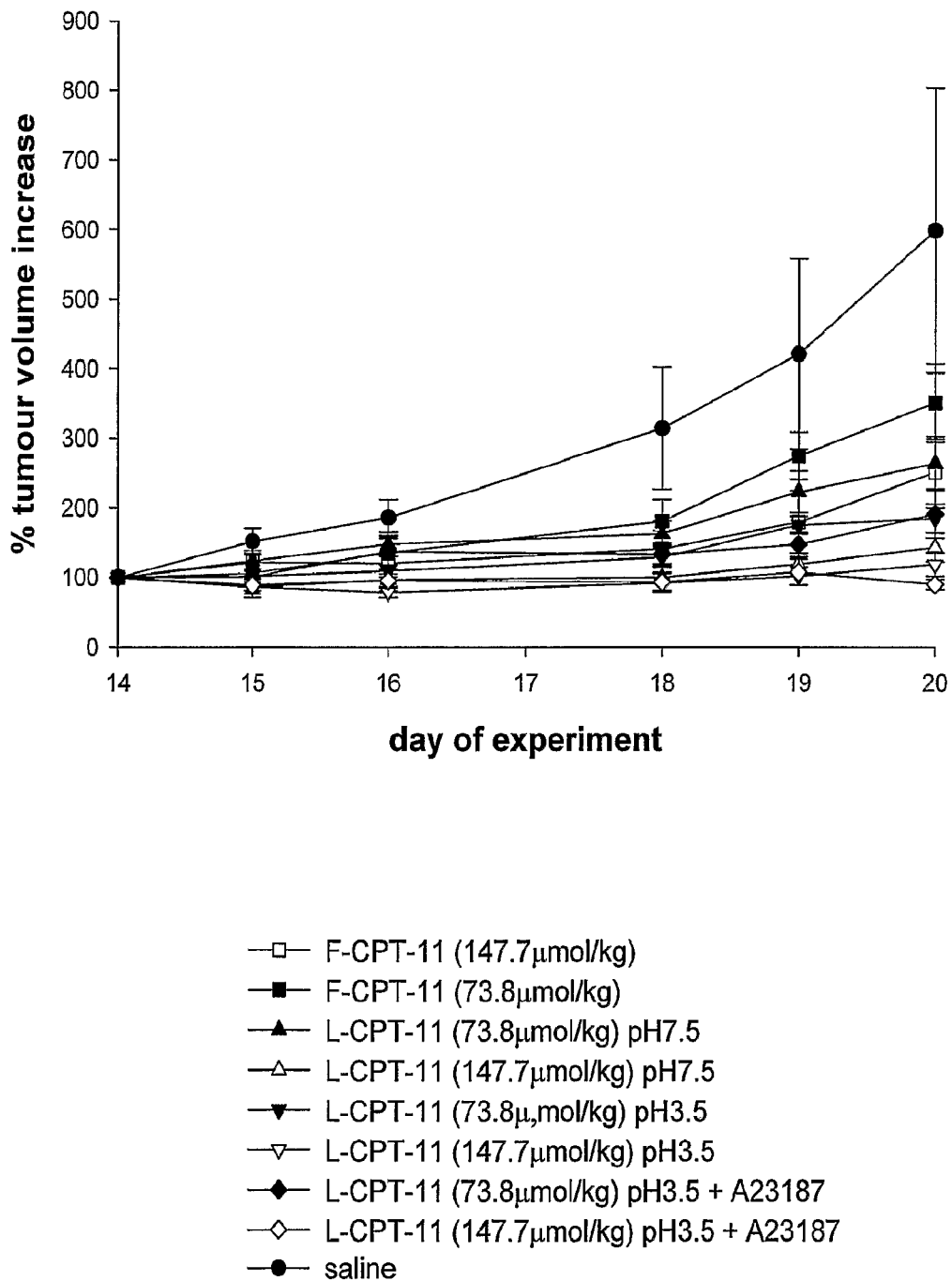
FIG. 11 is a graph showing percentage in s.c. LSI80 tumor volume following a single dose of free or encapsulated CPT-11.
Figure 12:
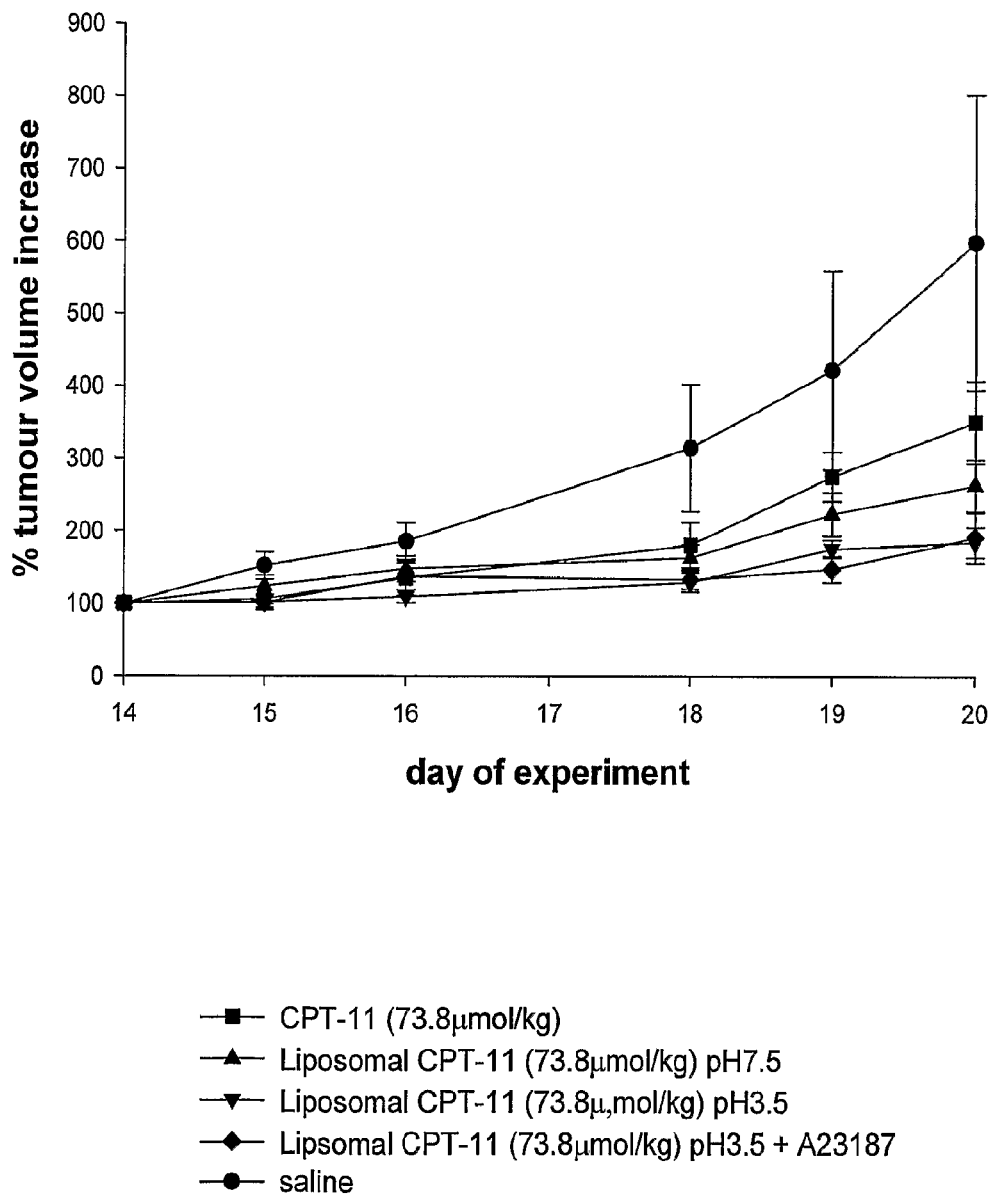
FIG. 12 is a graph showing percentage increase in tumor volume following a single 50 mg/kg dose of free or encapsulated CPT-11.
Figure 13:
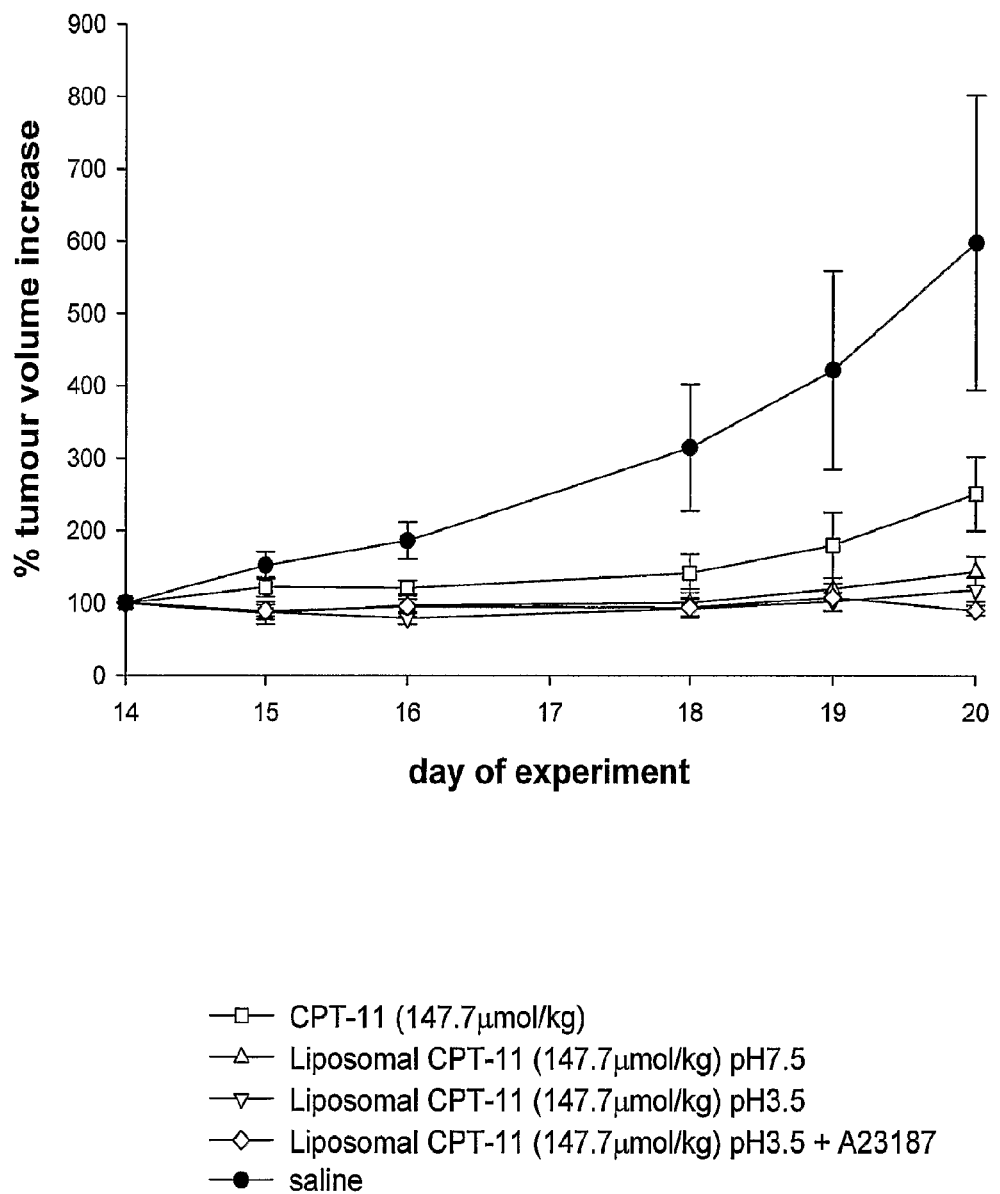
FIG. 13 is a graph showing percentage increase in tumor volume following a single 100 mg/kg dose of free or encapsulated CPT-11.
Figure 14:
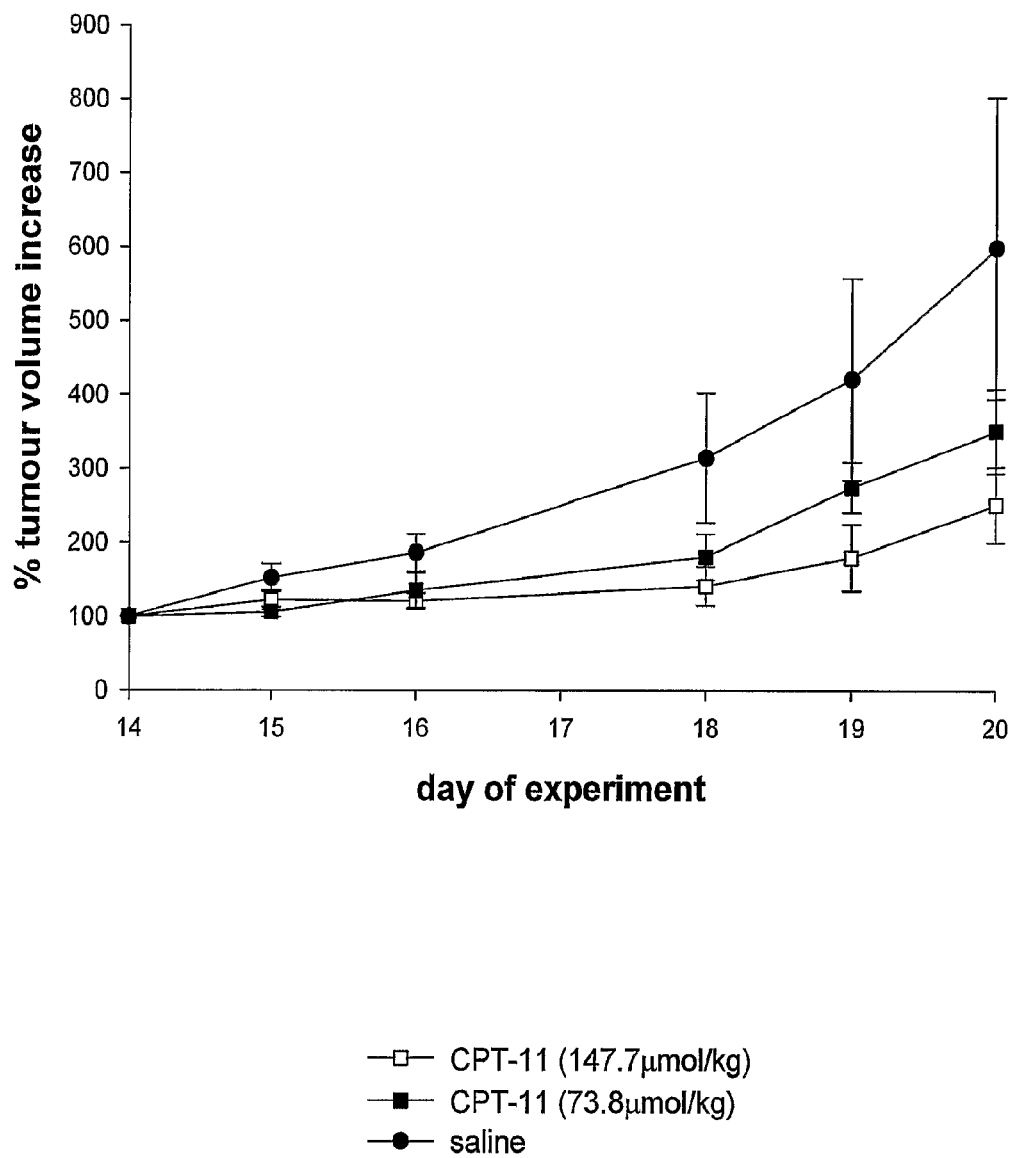
FIG. 14 is a graph showing percentage increase in tumor volume following a single dose of free CPT-11.
Figure 15:
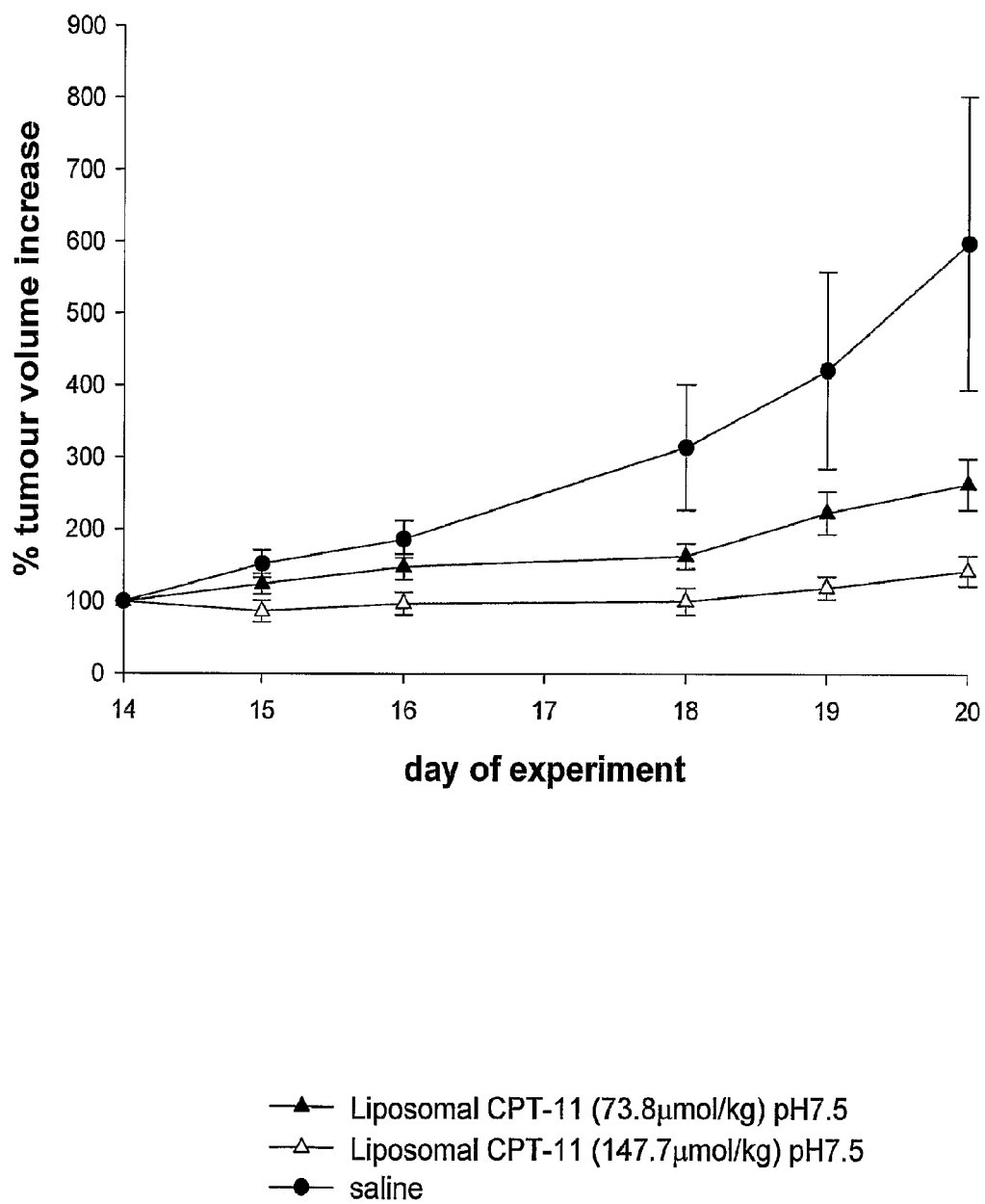
FIG. 15 is a graph showing percentage increase in tumor volume following a single dose of pH 7.5 encapsulated CPT-11.
Figure 16:
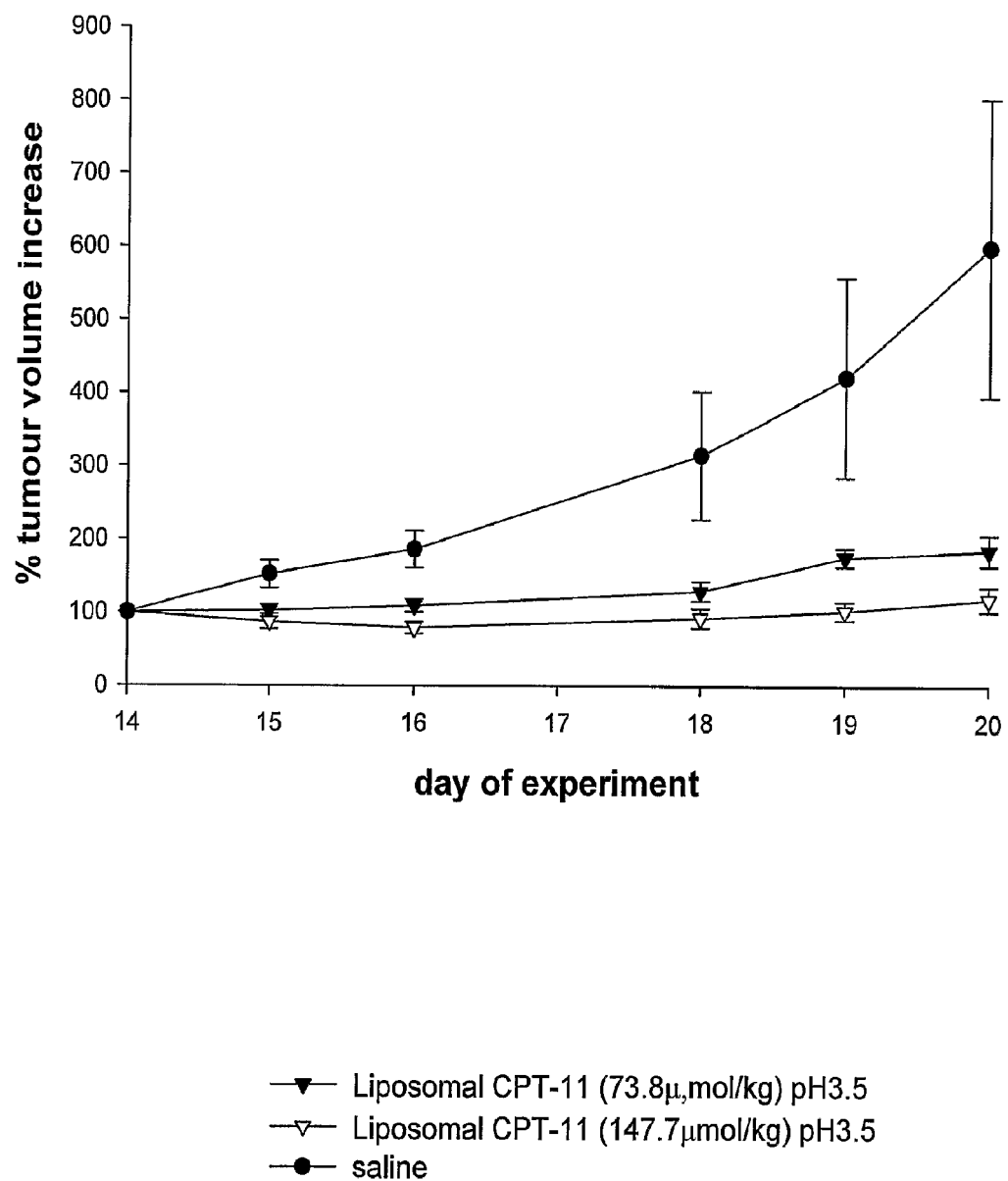
FIG. 16 is a graph showing percentage increase in tumor volume following a single dose of pH 3.5 encapsulated CPT-11.
Figure 17:
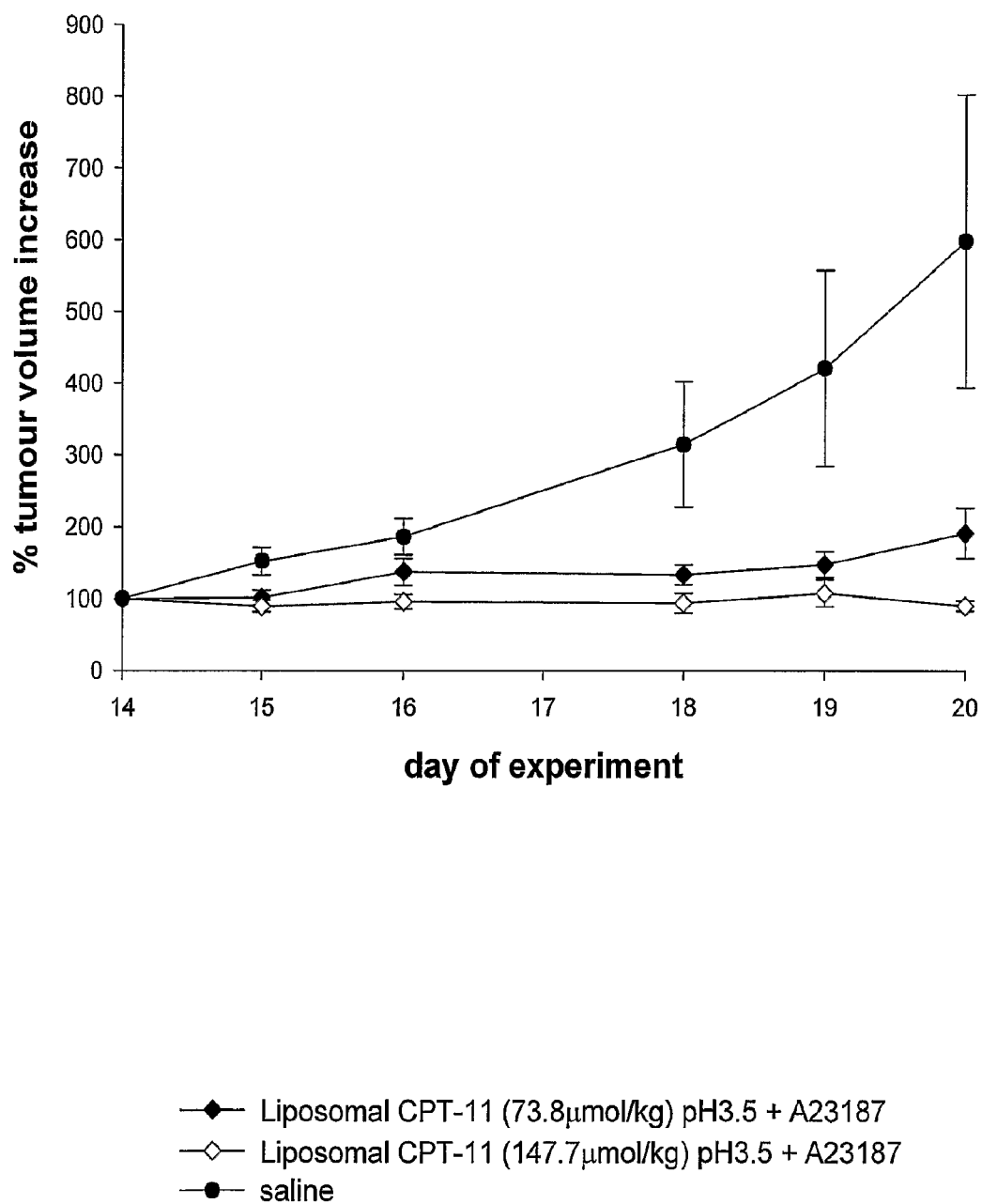
FIG. 17 is a graph showing percentage increase in tumor volume following a single dose of pH 3.5+ionophore encapsulated CPT-11.

Accounting for the effects of irinotecan on the excitation scans shown in FIG. 4C, the loading of this drug into Cu-containing liposomes at pH 7.5 resulted in no appreciable change in the scan when compared with the drug-free counterpart (FIG. 4B).

1.2.6 Irinotecan Lactone Ring Detection

Irinotecan was resolved on a CI 8 column (3.9×150 mm) using a mobile phase comprising 78% triethanolamine solution (3% v/v) and 22% acetonitrile. Drug was quantified by fluorescence (lexci=363 nm; lemiss=425 nm). Peak area analysis indicates that for liposomes containing the unbuffered CuSO4, 96% of irinotecan exists as the lactone form and 4% as the carboxylate form (FIG. 5). The equivalent values for liposomes possessing an interior buffer of CuSO4 pH 7.5 are 83% lactone and 17% carboxylate.

Irinotecan controls and liposomal samples were solubilized in CHC13:MeOH (1:1 v/v) and spotted on a TLC plate. The lactone and carboxy forms of the drug were separated by exposing the TLC plate initially to a mobile phase of CHC13:MeOH:acetone (9:3:1 v/v/v) followed by a mobile phase of butanohacetic acid:water:acetone (4:2:1:1 v/v/v/v). The drug was visualized under UV light and confirmed that irinotecan existed predominantly in the lactone form (FIG. 6).

1.2.7 In Vivo Liposome Stability Studies

Analysis of the liposome stability was determined by measuring free lipid and free drug levels in the plasma at specific timepoints (FIGS. 7-10). These results showed that $Cu^{2+}$ with ionophore A23187 at pH 3.5 provided superior drug retention in the liposomes versus use of $Mg^{2+}$ or in the absence of the ionophore or at pH 7.5 (see FIG. 9 and FIG. 10).

1.2.8 Efficacy Studies

The effect of encapsulating the drug irinotecan (CPT-11) on tumor volume is shown in FIGS. 11-17. The effects of encapsulation in the presence of $Cu^{2+}$ at pH 7.5 versus pH 3.5 versus pH 3.5 with ionophore were compared at two doses of irinotecan (CPT-11). Encapsulation at pH 3.5 or at pH 3.5 with ionophore both provided highly effective therapeutic regimes. A more detailed analysis (FIG. 18) showed that encapsulation in the presence of $Cu^{2+}$ at pH 3.5 in the presence of ionophore provided the longest growth delay for the tumour, highest log cell kill and superior cell kill at the lowest dose (50 mol/kg). In FIG. 18, T−C is the difference in days for a treatment tumour to increase in volume by 400% compared to control tumours; % Growth Delay=(T−C)/C×100, where C is the day of experiment when control tumour reaches 400%; Log Cell Kill=(T−C)/(3.32×Td), where Td is the tumour doubling time of control tumours; and % Cell Kill=$(1-(1/10^x))\times 100$, where x is the Log Cell Kill.

Taken together, these efficacy results show that the composition consisting of $Cu^{2+}$ with ionophore and irinotecan provides the most potent composition. This is consistent with the observations that this composition provides the best plasma stability.

Irinotecan loading efficiencies were >90% using liposomes with CuSO4. The inclusion of A23187 ionophore, to maintain a low internal pH, did not influence the copper-mediated loading behaviour, but strongly enhanced drug retention in liposomes when measured in plasma. Furthermore, HPLC and TLC indicate that encapsulated irinotecan exists predominately as the clinically-active lactone form regardless of the initial internal pH of the transition metal solution. This composition provides enhanced drug retention in plasma yielding increased drug exposure in vivo and resulting in enhanced efficacy for lower doses of irinotecan in the mouse xenograft tumor model.

In summary, irinotecan can be encapsulated into DSPC/Chol liposomes using transition metal $Cu^{2+}$ and an ionophore in a composition which provides excellent drug retention and superior efficacy in vivo.

Example 2.0

2.1 Plasma Drug Retention

FIGS. 19 and 20 illustrate drug to lipid ratios in the plasma following in vivo administration to Rag-2M mice. In each case the administered formulations consisted of the same liposome composition with different internal solutions as indicated in the figure legends. In the case of both the drug irinotecan (FIG. 19) and vinorelbine (FIG. 20) the formulation prepared by $Cu^{2+}$/A23187 drug loading technology demonstrated significantly better plasma drug retention as indicated by the higher relative drug-to-lipid ratios.

2.2 Pharmacokinetic Parameters of Different Irinotecan Treatments

FIG. 21 is a table similar to FIG. 18 summarizing pharmacokinetic parameters of different irinotecan treatments. The delay in tumour growth was most effective in the case of the formulation prepared by $Cu^{2+}$/A23187 drug loading technology. In FIG. 21, irinotecan plasma-area-under-the-curve (AUG) was calculated using WinNonLin pharmacokinetic software (noncompartmental model) following a single i.v. bolus dose administered to Rag-2M mice (n=3/timepoint). The irinotecan plasma mean residence time (MRT) was calculated using WinNonLin pharmacokinetic software (noncompartmental model) following a single i.v. bolus dose administered to Rag-2M mice (n=3/timepoint). The % growth delay was calculated following a single dose of irinotecan treatment administered to Rag-2M mice with established s.c. LSI 80 tumours (human colorectal carcinoma xenograft). % Growth Delay=(T−C)/C×100, where C is the day of experiment when control tumours reach 400% and T−C is the difference in days for a treatment tumour to increase in volume by 400% compared to control tumours. Efficacy values are not stated for liposomal irinotecan (unbuffered 300 mM MnSO4+A23187) because no head-to-head studies have been conducted. We have previously published efficacy data relating to this murine model and this liposome formulation (Messerer et al., Clin. Cancer Res. 10:6638-49, 2004).

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A composition comprising a liposome encapsulating a single therapeutic agent, wherein said therapeutic agent is loaded into said liposome in the presence of intra-liposomal copper ions and a divalent proton cation exchange ionophore within the lipid bilayer of said liposome, wherein said divalent proton cation exchange ionophore is A23187.

2. The composition as defined in claim 1, wherein said therapeutic agent is an anti-cancer drug.

3. The composition as defined in claim 2, wherein said drug is a topoisomerase inhibitor.

4. The composition as defined in claim 3, wherein said drug is a camptothecin or an analogue thereof.

5. The composition as defined in claim 4, wherein said drug is irinotecan.

6. The composition as defined in claim 5, wherein said irinotecan is predominately present in the lactone form.

7. The composition as defined in claim 2, wherein said drug binds to tubulin.

8. The composition as defined in claim 7, wherein said drug is a vinca alkaloid or a derivative thereof.

9. The composition as defined in claim 8, wherein said drug is selected from the group consisting of vinblastine, vincristine, vindesine and vinorelbine.

10. The composition as defined in claim 1, wherein said lipsosome comprises lipids selected from the group consisting of phosphoglycerides and sphingolipids.

11. The composition as defined in claim 10, wherein said lipids are selected from the group consisting of phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine and dilinoleoylphosphatidylcholine.

12. The composition as defined in claim 11, wherein said liposome comprises 1,2-distearoyl-sn-glycero-3-phosophocholine (DSPC)/Cholesterol.

13. A method for treating cancer in a subject comprising the step of administering the composition as defined in claim 1.

14. A liposomal formulation produced by a method comprising:
    (a) providing within the interior of said liposomes an intraliposomal solution comprising copper ions;
    (b) providing a divalent proton cation exchange ionophore for facilitating exchange of ions between said intraliposomal solution and an external solution, wherein said divalent proton cation exchange ionophore is A23187; and
    (c) providing said therapeutic agent in said external solution, wherein said therapeutic agent diffuses into said interior and is encapsulated within said liposomes, and wherein the presence of said copper ions enhances the retention of said therapeutic agent therein,
    wherein said ionophore is added to said external solution prior to providing said therapeutic agent in said external solution.

15. The formulation as defined in claim 14, wherein said ionophore exchanges said copper ions in divalent form from said interior with protons in said external solution.

16. The formulation as defined in claim 14, wherein said therapeutic agent is an anti-cancer drug.

17. The formulation as defined in claim 16, wherein said drug is a topoisomerase inhibitor.

18. The formulation as defined in claim 17, wherein said drug is a camptothecin or an analogue thereof.

19. The formulation as defined in claim 18, wherein said drug is irinotecan.

20. The formulation as defined in claim 16, wherein said drug binds to tubulin.

21. The formulation as defined in claim 20, wherein said drug is a vinca alkaloid or a derivative thereof.

22. The formulation as defined in claim 21, wherein said drug is selected from the group consisting of vinblastine, vincristine, vindesine and vinorelbine.

23. The formulation as defined in claim 14, wherein said lipsosome comprises lipids selected from the group consisting of phosphoglycerides and sphingolipids.

24. The formulation as defined in claim 23, wherein said lipids are selected from the group consisting of phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine and dilinoleoylphosphatidylcholine.

25. The formulation as defined in claim 24, wherein said liposome comprises 1,2-distearoyl-sn-glycero-3-phosophocholine (DSPC)/Cholesterol.

26. A composition comprising a liposomal formulation of claim 14.

* * * * *